United States Patent
Rivas et al.

(10) Patent No.: US 10,812,045 B2
(45) Date of Patent: Oct. 20, 2020

(54) BAW SENSOR WITH ENHANCED SURFACE AREA ACTIVE REGION

(71) Applicant: Qorvo US, Inc., Greensboro, NC (US)

(72) Inventors: Rio Rivas, Bend, OR (US); Craig Andrus, Bend, OR (US)

(73) Assignee: Qorvo Biotechnologies, LLC, Plymouth, MN (US)

( * ) Notice: Subject to any disclaimer, the term of this patent is extended or adjusted under 35 U.S.C. 154(b) by 345 days.

(21) Appl. No.: 15/339,062

(22) Filed: Oct. 31, 2016

(65) Prior Publication Data

US 2017/0134002 A1 May 11, 2017

Related U.S. Application Data

(60) Provisional application No. 62/252,688, filed on Nov. 9, 2015.

(51) Int. Cl.
*H03H 9/17* (2006.01)
*G01N 29/24* (2006.01)
(Continued)

(52) U.S. Cl.
CPC ......... *H03H 9/17* (2013.01); *B01L 3/502707* (2013.01); *B01L 3/502715* (2013.01);
(Continued)

(58) Field of Classification Search
CPC ............. B01L 3/50273; B01L 2200/10; B01L 2300/0645; B01L 2300/0816;
(Continued)

(56) References Cited

U.S. PATENT DOCUMENTS

| 4,640,756 A | 2/1987 | Wang et al. |
| 7,468,608 B2 | 12/2008 | Feucht et al. |

(Continued)

FOREIGN PATENT DOCUMENTS

| DE | 10 2006 004 448 B3 | 10/2007 |
| WO | WO 2006/063437 A1 | 6/2006 |

(Continued)

OTHER PUBLICATIONS

Qorvo US, Inc., "Summary of Sales Activity of Predecessor to Applicant Concerning Tilted C-Axis Aluminum Nitride Products," Unpublished, Jan. 10, 2017, 1 page.

(Continued)

*Primary Examiner* — Robert J Eom
(74) *Attorney, Agent, or Firm* — Mueting Raasch Group

(57) ABSTRACT

A bulk acoustic wave MEMS resonator device includes at least one functionalization (e.g., specific binding or non-specific binding) material arranged over a top side electrode, with at least one patterned enhanced surface area element arranged between a lower surface of the top side electrode and the functionalization material. The at least one patterned enhanced surface area element increases non-planarity of the at least one functionalization material, thereby providing a three-dimensional structure configured to increase sensor surface area and reduce analyte diffusion distance, and may also promote fluid mixing. Methods for biological and chemical sensing, and methods for forming MEMS resonator devices and fluidic devices are further disclosed.

16 Claims, 11 Drawing Sheets

(51) Int. Cl.
    *B01L 3/00*     (2006.01)
    *G01N 29/02*     (2006.01)
    *G01N 29/22*     (2006.01)
    *G01N 33/543*     (2006.01)
    *H03H 3/02*     (2006.01)

(52) U.S. Cl.
    CPC ...... *B01L 3/502761* (2013.01); *G01N 29/022* (2013.01); *G01N 29/222* (2013.01); *G01N 29/2437* (2013.01); *G01N 33/5438* (2013.01); *H03H 3/02* (2013.01); *B01L 2200/12* (2013.01); *B01L 2300/0645* (2013.01); *B01L 2300/0887* (2013.01); *G01N 2291/0255* (2013.01); *G01N 2291/0256* (2013.01); *G01N 2291/0426* (2013.01); *H03H 2003/027* (2013.01)

(58) Field of Classification Search
    CPC ..... B01L 2300/0887; B01L 2400/0496; G01N 29/022; G01N 29/036; G01N 29/222; G01N 33/54386; G01N 2291/0255; G01N 2291/0256; G01N 2291/0426; G01N 2610/00; H03H 9/17; H03H 9/175
    See application file for complete search history.

(56) References Cited

U.S. PATENT DOCUMENTS

| | | | |
|---|---|---|---|
| 7,802,466 | B2 | 9/2010 | Whalen et al. |
| 8,409,875 | B2 | 4/2013 | Johal et al. |
| 9,096,823 | B1 | 8/2015 | Branch et al. |
| 2006/0054941 | A1* | 3/2006 | Lu ........................ C12Q 1/6825 257/252 |
| 2006/0125489 | A1 | 6/2006 | Feucht et al. |
| 2006/0222568 | A1* | 10/2006 | Wang ..................... B82Y 15/00 422/70 |
| 2007/0210349 | A1 | 9/2007 | Lu et al. |
| 2010/0088039 | A1 | 4/2010 | Yang et al. |
| 2015/0293060 | A1 | 10/2015 | Jacobsen |
| 2017/0110300 | A1 | 4/2017 | McCarron et al. |
| 2017/0120242 | A1 | 5/2017 | Rivas et al. |
| 2017/0122911 | A1 | 5/2017 | McCarron et al. |
| 2017/0122936 | A1 | 5/2017 | Rivas et al. |

FOREIGN PATENT DOCUMENTS

| | | |
|---|---|---|
| WO | WO 2007/123539 A1 | 11/2007 |
| WO | PCT/US2016/059312 | 10/2016 |
| WO | PCT/US2016/059327 | 10/2016 |
| WO | WO 2017/075344 A1 | 5/2017 |
| WO | WO 2017/075354 A1 | 5/2017 |

OTHER PUBLICATIONS

Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.
Groner, M. D. et al., "Gas diffusion barriers on polymers using $Al_2O_3$ atomic layer deposition," Applied Physics Letters, vol. 88, Jan. 31, 2006, 051907-1 to 051907-3.
Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.
Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.
Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.
Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.
Nguyen, Nam-Trung et al., "Micromixers—a review," Journal of Micromechanics and Microengineering, vol. 15, Dec. 8, 2004, pp. R1-R16.
Nirschl, Martin et al., "CMOS-Integrated Film Bulk Acoustic Resonators for Label-Free Biosensing," Sensors, vol. 10, No. 5, Apr. 27, 2010, pp. 4180-4193.
Stroock, Abraham D. et al., "Chaotic Mixer for Microchannels," Science, vol. 295, Jan. 25, 2002, pp. 647-651.
Suh, Yong Kweon et al., "A Review on Mixing in Microfluidics," Micromachines, vol. 1, No. 3, Sep. 30, 2010, pp. 82-111.
Zhou, Yan et al., "Interfacial Structures and Properties of Organic Materials for Biosensors: An Overview," Sensors, vol. 12, Nov. 6, 2012, pp. 15036-15062.
U.S. Appl. No. 15/293,063, filed Oct. 13, 2016, McCarron et al.
Author unknown, "Acoustic Wave Sensors," Vectron International, Date Unknown, 44 pages, <www.sengenuity.com/tech_ref/AWS_WebVersion.pdf>.
Bjurstrom et al., "Design and Fabrication of Temperature Compensated Liquid FBAR Sensors," 2006, *IEEE Ultrasonics Symposium*, 894-897.
Chapter 21, Lou et al., *Modeling and Measurements Methods for Acoustic Waves and for Acoustic Microdevices*, 2013, "Acoustic Wave Based Microfluidics and Lab-on-a-Chip," 515-56.
Chen et al., "Characteristics of Dual Mode AlN Thin Film Bulk Acoustic Wave Resonators," 2008, *IEEE*, 609-14.
Chen et al., "The Liquid Sensor Using Thin Film Bulk Acoustic Resonator with C-Axis Tilted AlN Films," *Journal of Nanomaterials*, 2003:1-8.
Fan et al., "An adaptive feedback circuit for MEMS resonators," Mar. 1, 2011, *Journal of Micromechanics and Microengineering*, 21:1-10.
International Patent Application No. PCT/US2016/059677, filed Oct. 31, 2016; International Search Report / Written Opinion dated May 18, 2017; 11 pages.
Link, "Study and realization of shear wave mode solidly mounted film bulk acoustic resonators (FBAR) made of c-axiz inclined zinc oxide (ZnO) thin films: application as gravimetric sensors in liquid environments," Sep. 14, 2006, Thesis, 225 pages.
Miller, "The Stokes-Einstein Law for Diffusion in Solution," *Proceedings of the Royal Society of London. Series A, Containing Papers of a Mathematical and Physical Character* (1905-1934), Jan. 1924, 106(70):724-49.
Montagut, Yeison et al. "QCM Technology in Biosensors," Biosensors—Emerging Materials and Applications, Chapter 9, 2011, INTECH Open Access Publisher, pp. 153-178.
Qin et al., "Analytical Study of Dual-Mode Thin Film Bulk Acoustic Resonators (FBARs) Based on ZnO and AlN Films with Tilted c-Axis Orientation," Aug. 2010, *IEEE Transactions of Ultrasonics, Ferroelectrics, and Frequency Control*, 57(8):1840-53.
Ramakrishnan, et al., "Resonant Frequency Characteristics of a SAW Device Attached to Resonating Micropillars," 2012, *Sensors*, 12(4):3789-97.
Yu et al, Ultra Temperature-Stable Bulk-Acoustic-Wave Resonators with SiO2 Compensation Layer, Oct. 2007, *IEEE Transactions of Ultrasonics, Ferroelectrics, and Frequency Control*, 54(10):2102-09.
Zhang et al., "A Microfluidic Love-Wave Biosensing Device for PSA Detection Based on an Aptamer Beacon Probe," 2015, *Sensors*, 15:13839-850.
U.S. Appl. No. 62/247,233, filed Oct. 28, 2015, Rivas.
U.S. Appl. No. 62/248,392, filed Oct. 30, 2015, Rivas.
U.S. Appl. No. 62/248,397, filed Oct. 30, 2015, McCarron et al.
U.S. Appl. No. 15/337,338, filed Oct. 28, 2016, Rivas et al.
U.S. Appl. No. 15/337,429, filed Oct. 28, 2016, Rivas et al.
U.S. Appl. No. 15/339,022, filed Oct. 31, 2016, McCarron et al.

(56) References Cited

OTHER PUBLICATIONS

International Patent Application No. PCT/US2016/059312, filed Oct. 28, 2016; International Search Report / Written Opinion dated Feb. 13, 2017; 12 pages.
International Patent Application No. PCT/US2016/059312, filed Oct. 28, 2016; International Preliminary Report on Patentability dated May 11, 2018; 8 pages.
International Patent Application No. PCT/US2016/059327, filed Oct. 28, 2016; International Search Report / Written Opinion dated Feb. 13, 2017; 15 pages.
International Patent Application No. PCT/US2016/059327, filed Oct. 28, 2016; International Preliminary Report on Patentability dated May 11, 2018; 9 pages.
International Patent Application No. PCT/US2016/059677, filed Oct. 31, 2016; International Preliminary Report on Patentability dated May 24, 2018; 9 pages.
Fu et al., "Aluminium Nitride thin Film Acoustic Wave Device for Microfluidic and Biosensing Applications," Sep. 1, 2010, *Acoustic Waves*, retrieved on Nov. 14, 2016 from the Internet. Retrieved from the Internet: <URL :https://www/researchgate/net/profile/MPY_Desmulliez/publication/267951195_Aluminium_Nitride_thin_Film-Acoustin_Wave_Device_for_Microfluidic_and_Biosensing_Applications/links/5450dd8b0cf295b561637e62.pdf>; 263-98pgs.
Katardjiev et al., "Recent developments in thin film electro-acoustic technology for biosensor applications," Oct. 19, 2011, *Vacuum*, 86(5):520-31.
"The Laser MicroJet® Technology: A Simple Principle," Synova: Cool Last Micro-Machining, Feb. 17, 2015; 8 pages.
Lee et al., "Microfluidic Mixing: A Review," May 18, 2011, *International Journal of Molecular Sciences*, 12:3263-87.
Luo, et al., Chapter 21, "Acoustic Wave Based Microfluidics and Lab-on-a-Chip," *Modeling and Measurement Methods for Acoustic Waves and for Acoustic Microdevices*, InTech, Aug. 28, 2013, pp. 515-556.
Rabus et al., "A high sensitivity open loop electronics for gravimetric acoustic wave-based sensors," Jun. 2013, *IEEE Transactions on Ultrasonics, Ferroelectrics, and Frequency Control*, 60(6):1219-1226.
Suh et al., "A Review on Mixing in Microfluidics," Sep. 30, 2010, *Micromachines*, 1(3):82-111.
Through Silicon Vias (TSV) for backside electrical connection are common in devices https://en.wikipedia.org/wiki/Through-silicon_via.
Voiculescu, et al., "Acoustic wave based MEMS devices for biosensing applications", 2012, *Biosensors and Bioelectronics*, 33:1-9, Published online Jan. 16, 2012.
Wingqvist, et al., "Shear mode AlN thin film electro-acoustic resonant sensor operation in viscous media", 2007, *Sensors and Actuators B*, 123:466-473. Published online Nov. 2, 2006.
Zhang, et al., "A single-chip biosensing platform integrating FBAR sensor with digital microfluidic device", *2014 IEEE International Ultrasonics Symposium Proceedings*, 2014, 3 pages.
Xu et al., "In-Liquid Quality Factor Improvement for Film Bulk Acoustic Resonators by Integration of Microfluidic Channels," Jun. 2009, *IEEE Electronic Device Letters*, 30(6): 647-49.

* cited by examiner

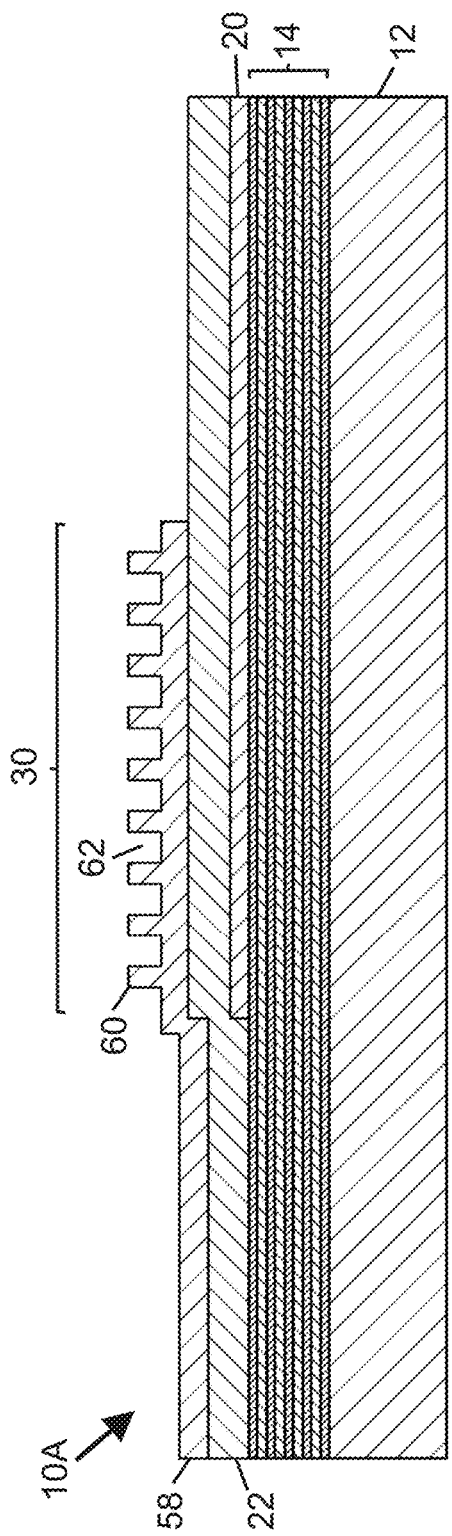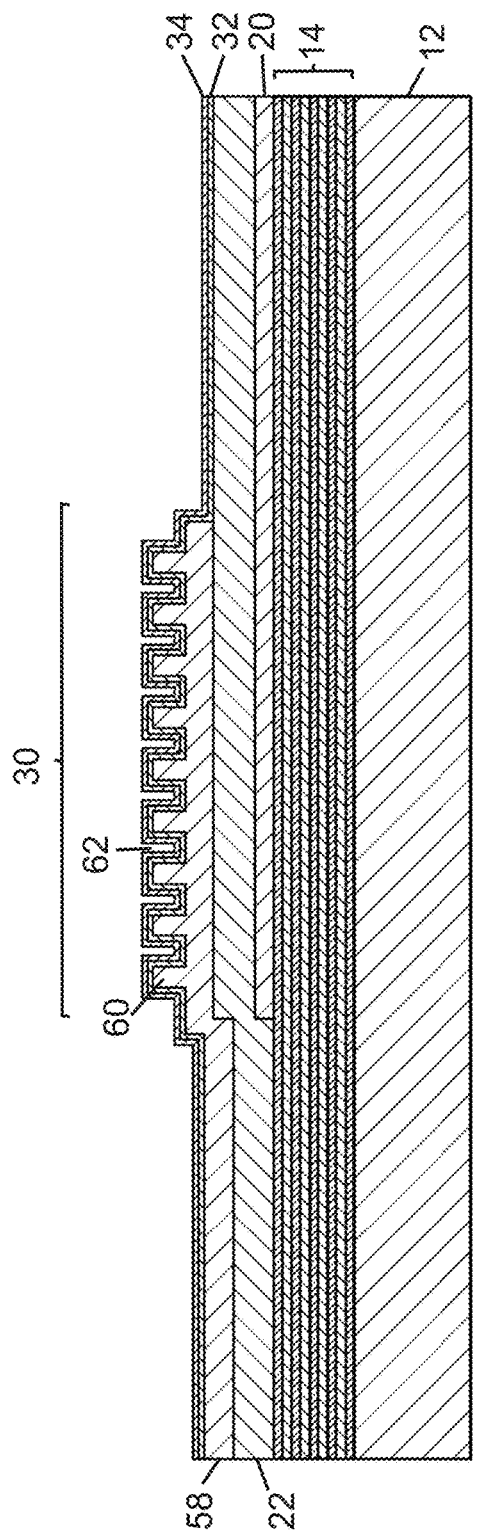
FIG. 5A
FIG. 5B

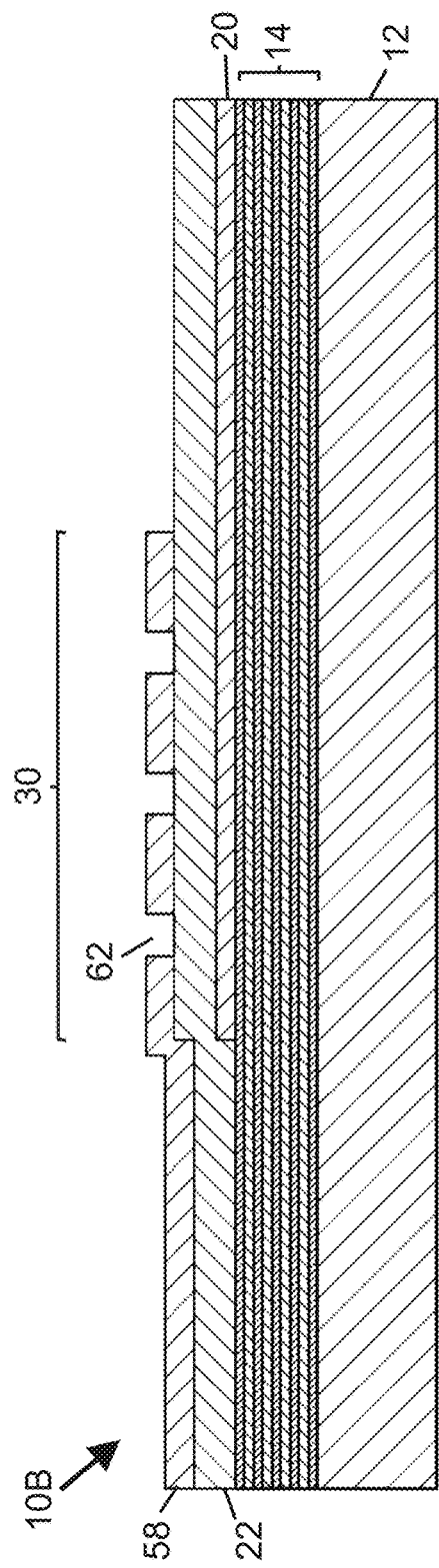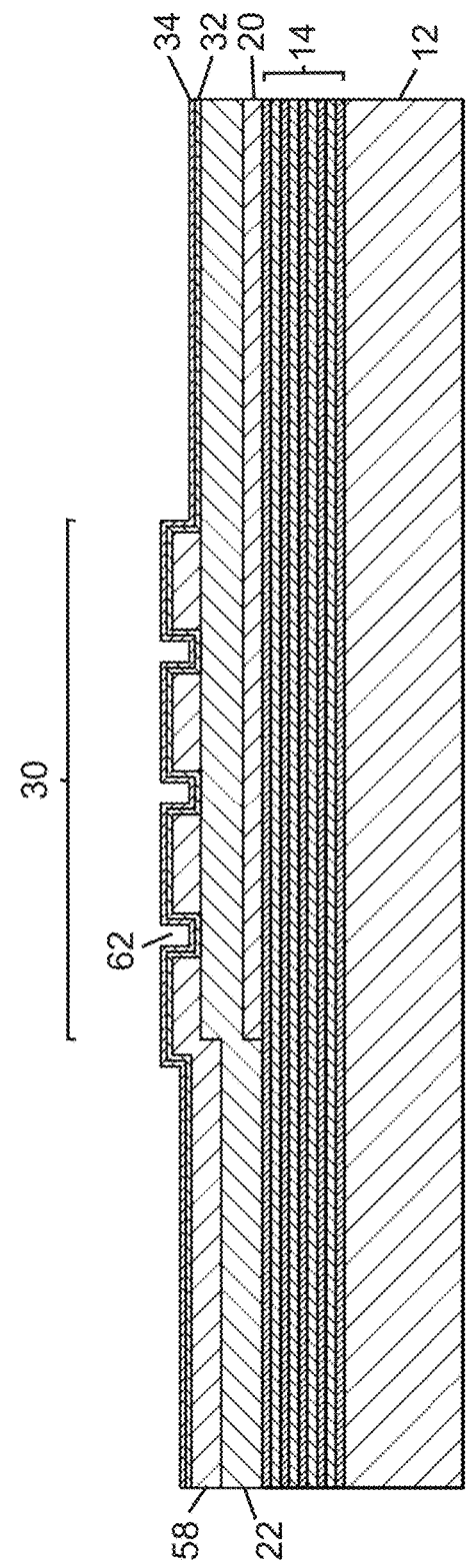

BAW SENSOR WITH ENHANCED SURFACE AREA ACTIVE REGION

STATEMENT OF RELATED APPLICATIONS

This application is a non-provisional of provisional patent application Ser. No. 62/252,688, filed Nov. 9, 2015, the disclosure of which is hereby incorporated herein by reference in its entirety. Subject matter disclosed herein also relates to U.S. patent application Ser. No. 15/339,022, filed Oct. 31, 2016, now U.S. Pat. No. 10,292,704, the contents of which are hereby incorporated by reference as if set forth fully herein.

TECHNICAL FIELD

The present disclosure relates to fluidic devices incorporating acoustic resonators, including fluidic devices and related systems suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the specific binding material, thereby altering the mass being vibrated by the acoustic wave and altering the wave propagation characteristics (e.g., velocity, thereby altering resonance frequency). Changes in velocity can be monitored by measuring the frequency, magnitude, or phase characteristics of the acoustic wave device, and can be correlated to a physical quantity being measured.

In the case of a piezoelectric crystal resonator, an acoustic wave may embody either a bulk acoustic wave (BAW) propagating through the interior of a substrate, or a surface acoustic wave (SAW) propagating on the surface of the substrate. SAW devices involve transduction of acoustic waves (commonly including two-dimensional Rayleigh waves) utilizing interdigital transducers along the surface of a piezoelectric material, with the waves being confined to a penetration depth of about one wavelength. BAW devices typically involve transduction of an acoustic wave using electrodes arranged on opposing top and bottom surfaces of a piezoelectric material. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes, as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof.

Typically, BAW devices are fabricated by micro-electromechanical systems (MEMS) fabrication techniques owing to the need to provide microscale features suitable for facilitating high frequency operation. In the context of biosensors, functionalization materials (e.g., specific binding materials; also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing.

Under typical operating conditions, flows in microfluidic channels (also termed "microchannels") are laminar. Fluids in laminar flow tend to follow parallel streamline paths, such that the chaotic fluctuations of velocity that tend to homogenize fluids in turbulent flows are absent. Multiple fluids introduced in a standard microfluidic channel generally will not mix with each other, except at a common interface between the fluids via diffusion, and the diffusion process is typically slow compared with the flow of fluid along a principal axis of a microfluidic channel. The same principles that inhibit rapid mixing of fluids flowing under laminar conditions in a microfluidic channel also affect the distribution of analytes contained in one or more fluids flowing within a microfluidic channel. Fick's first law of diffusion states that flux moves from regions of high concentration to regions of low concentration. Secondarily, the flux rate is proportional to the concentration gradient difference. In a volume of fluid containing an analyte and advancing in a horizontal direction through a microfluidic channel having functionalization material arranged along a bottom surface of the microfluidic channel, the fluid volume may be modeled as a moving "stack" of horizontal fluid layers. Even if it is assumed that analyte concentration is constant in each layer of the stack forming the fluid volume upon entering the microfluidic channel, following passage of the fluid volume over the functionalization material, a lowermost fluid layer of the stack will exhibit reduced or depleted analyte concentration due to binding of analyte with the functionalization material. But since diffusion is slow in a direction perpendicular to the direction of fluid flow through the microfluidic channel, and analyte needs to diffuse to a surface bearing functionalization material to bind, analyte present in fluid layers other than the lowermost fluid layer may not be available for binding with the functionalization material along the bottom surface of the microfluidic channel within a reasonable period of time.

Thus, conventional biochemical sensing devices may suffer from inconsistent distribution of target species in a sample and/or a low rate of analyte binding that may extend the time necessary to complete measurement of a particular sample. Accordingly, there is a need for fluidic devices incorporating BAW resonator structures, such as for biosensing or biochemical sensing applications, that overcome limitations associated with conventional devices.

SUMMARY

The present disclosure provides a micro-electrical-mechanical system (MEMS) resonator device including a piezoelectric material arranged between a top side electrode and a bottom side electrode, a functionalization material (or at least one functionalization material) arranged over the top side electrode, and at least one patterned enhanced surface area element arranged between a lower surface of the top side electrode and the functionalization material. The at least one patterned enhanced surface area element is configured to increase non-planarity of the functionalization material, thereby providing a three-dimensional structure configured to increase sensor surface area and reduce analyte diffusion distance to improve sensor performance by enabling capture of an increased amount of analyte. Additionally, the at least one patterned enhanced surface area element may promote passive mixing of analyte-containing fluid flowing over such element(s). One or more layers (e.g., a hermeticity layer, an interface layer, and/or a self-assembled monolayer) may be arranged between the top side electrode and the functionalization material. In certain embodiments, one or more patterned enhanced surface area elements may be embodied in: a patterned top side electrode, a patterned photoimageable material, or another patterned layer (e.g., a hermeticity layer or an interface layer) arranged between the top side electrode and the functionalization material. Further provided are fluidic devices incorporating MEMS resonator devices disclosed herein, as well as methods for biological and chemical sensing, and methods for forming MEMS resonator devices and fluidic devices.

In one aspect, a micro-electrical-mechanical system (MEMS) resonator device includes: a substrate; a bulk acoustic wave resonator structure arranged over at least a portion of the substrate, the bulk acoustic wave resonator structure including a piezoelectric material, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region; at least one functionalization material arranged over at least a portion of the active region; and at least one patterned enhanced surface area element arranged between a lower surface of the top side electrode and the at least one functionalization material, and configured to increase non-planarity of the at least one functionalization material.

In certain embodiments, the at least one patterned enhanced surface area element comprises at least one of (i) a plurality of upwardly protruding portions of the top side electrode or (ii) a plurality of recesses defined in the top side electrode. In certain embodiments, the at least one patterned enhanced surface area element comprises an electrically conductive material.

In certain embodiments, the at least one patterned enhanced surface area element comprises a patterned photoimageable material arranged between the top side electrode and the at least one functionalization material.

In certain embodiments, the at least one patterned enhanced surface area element comprises a metal that is arranged over the top side electrode and is compositionally different from a composition of the top side electrode. In certain embodiments, the at least one patterned enhanced surface area element comprises a dielectric material arranged over the top side electrode.

In certain embodiments, the top side electrode comprises a non-noble metal, and the MEMS resonator device further comprises a hermeticity layer arranged between the top side electrode and the at least one functionalization material. In certain embodiments, the at least one patterned enhanced surface area element may include at least one of (i) a plurality of upwardly protruding portions of the hermeticity layer or (ii) a plurality of recesses defined in the hermeticity layer.

In certain embodiments, the MEMS resonator device further comprises an interface layer arranged between the top side electrode and the at least one functionalization material. In certain embodiments, the at least one patterned enhanced surface area element may include at least one of (i) a plurality of upwardly protruding portions of the interface layer or (ii) a plurality of recesses defined in the interface layer. In certain embodiments, the MEMS resonator device further comprises a self-assembled monolayer arranged between the interface layer and the at least one functionalization material.

In certain embodiments, the MEMS resonator device further comprises a self-assembled monolayer arranged between the top side electrode and the at least one functionalization material.

In certain embodiments, the piezoelectric material comprises a hexagonal crystal structure piezoelectric material comprising a c-axis having an orientation distribution that is predominantly non-parallel to normal of a face of the substrate.

In certain embodiments, a peripheral boundary of the active region defines a two-dimensional area; and the at least one functionalization material is arranged over the at least one patterned enhanced surface area element over a surface area that is at least 10% greater than the two-dimensional area.

In certain embodiments, the MEMS resonator device further comprises at least one acoustic reflector element arranged between the substrate and the bulk acoustic wave resonator structure.

In certain embodiments, the substrate defines a recess, and the MEMS resonator device further comprises a support layer arranged between the bulk acoustic wave resonator structure and the recess, wherein the active region is arranged over at least a portion of the support layer and at least a portion of the recess.

In another aspect, a fluidic device comprises the MEMS resonator device as disclosed herein, and a fluidic passage containing the active region and arranged to conduct a flow of liquid to contact the at least one functionalization material.

In another aspect, a method for biological or chemical sensing includes: supplying a fluid containing an analyte into the fluidic passage of the fluidic device as disclosed herein, wherein said supplying is configured to cause at least some of the analyte to bind to the at least one functionalization material; inducing a bulk acoustic wave in the active region; and sensing a change in at least one of a frequency property, a phase property, or an amplitude magnitude property of the bulk acoustic wave resonator structure to indicate at least one of presence or quantity of analyte bound to the at least one functionalization material.

In another aspect, a method for fabricating a microelectrical-mechanical system (MEMS) resonator device comprising an active region and at least one functionalization material arranged over at least a portion of the active region includes multiple steps. The method includes: forming a top side electrode over a portion of a piezoelectric material arranged over a substrate, with a bottom side electrode being arranged between the piezoelectric material and the substrate, wherein a portion of the piezoelectric material is arranged between the top side electrode and the bottom side electrode to form the active region; defining at least one patterned enhanced surface area element arranged between a lower surface of the top side electrode and the at least one functionalization material, wherein at least a portion of the at least one patterned enhanced surface area element is registered with the active region; and depositing the at least one functionalization material over the at least one patterned enhanced surface area element, wherein at least a portion of the at least one functionalization material is registered with the active region, and wherein the at least one patterned enhanced surface area element is configured to increase non-planarity of the at least one functionalization material.

In certain embodiments, the defining of at least one patterned enhanced surface area element comprises removing material over or from the top side electrode via a subtractive material removal process. In certain embodiments, the subtractive material removal process comprises etching. In certain embodiments, the defining of at least one patterned enhanced surface area element comprises addition of material over or to the top side electrode via an additive manufacturing process. In certain embodiments, the defining of at least one patterned enhanced surface area element comprises patterning of photoimageable material over at least a portion of the top side electrode, and the at least one functionalization material is deposited over at least a portion of the photoimageable material. In certain embodiments, a peripheral boundary of the active region defines a two-dimensional area; and the at least one functionalization material is arranged over the at least one patterned enhanced surface area element over a surface area that is at least 10% greater than the two-dimensional area. In certain embodiments, the method further includes forming at least one wall over a portion of the MEMS resonator device and defining a fluidic passage containing the active region.

In another aspect, a fluidic device includes: a channel arranged to receive a fluid; and a bulk acoustic wave resonator structure arranged between a substrate and a surface bounding at least a portion of the channel, wherein the bulk acoustic wave resonator structure includes (i) a piezoelectric material comprising a c-axis having an orientation distribution that is predominantly non-parallel to normal of a face of the substrate, (ii) a bottom side electrode arranged between the piezoelectric material and the substrate, and (iii) a top side electrode arranged between the piezoelectric material and the channel, wherein at least a portion of the piezoelectric material is arranged between the bottom side electrode and the top side electrode to form an active region. The top side electrode includes at least one recess that is defined in a surface of the top side electrode proximate to the channel. The at least one channel may be provided in various configurations as disclosed herein. For example, in certain embodiments, the at least one recess comprises a first recess and a second recess, wherein the second recess is laterally displaced and non-intersecting relative to the first recess.

In certain embodiments, the fluidic device further includes at least one functionalization material arranged over at least a portion of the top side electrode, wherein the at least one functionalization material is arranged to contact the fluid received by the channel. In certain embodiments, a self-assembled monolayer, an interface layer, and/or a hermeticity layer may be provided between the at least one functionalization material and the piezoelectric material and/or top side electrode of the bulk acoustic wave resonator structure.

In another aspect, any one or more aspects or features of one or more embodiments may be combined with aspects or features of one or more other embodiments for additional advantage, unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 5A is a schematic cross-sectional view of a portion of a BAW MEMS resonator device similar to the device of FIG. 1, but including a top side electrode embodying a patterned enhanced surface area element with multiple upwardly extending protrusions separated by recesses.

FIG. 5B is a schematic cross-sectional view of the BAW MEMS resonator device portion of FIG. 5A, with a hermeticity layer and an interface layer arranged over the top side electrode and over a piezoelectric material.

FIG. 10A is a schematic cross-sectional view of a portion of a bulk acoustic wave (BAW) resonator structure according to one embodiment, with the top side electrode embodying a patterned enhanced surface area element including an active region with a plurality of grooves or recesses defined in a top side electrode.

FIG. 10B is a schematic cross-sectional view of the portion of a BAW resonator structure of FIG. 10A following formation of multiple layers over the piezoelectric material and top side electrode.

DETAILED DESCRIPTION

Figure 1:
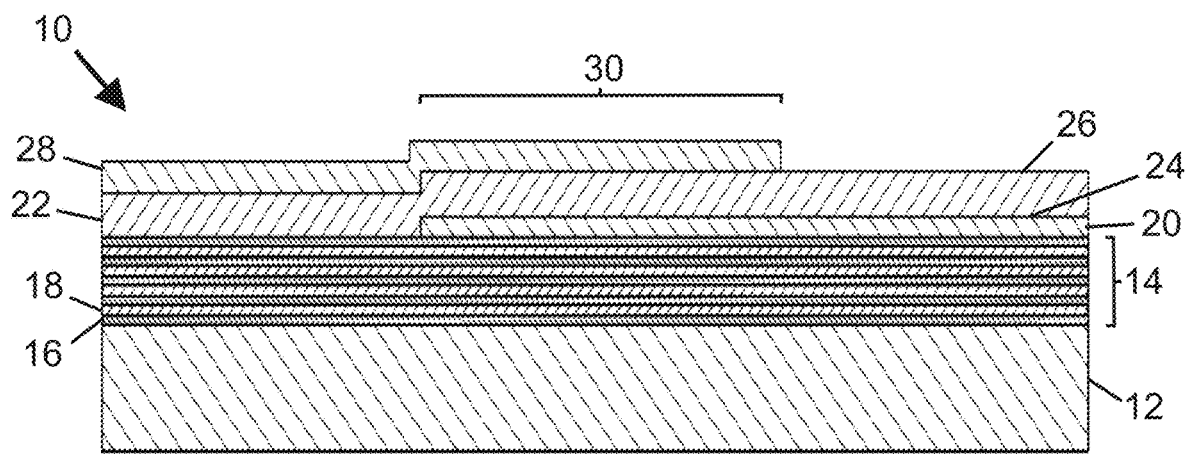
FIG. 1 is a schematic cross-sectional view of a portion of a bulk acoustic wave (BAW) MEMS resonator device usable with embodiments disclosed herein, including an active region with a piezoelectric material arranged between overlapping portions of a top side electrode and a bottom side electrode.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper"

element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure includes a micro-electrical-mechanical system (MEMS) resonator device including a piezoelectric material arranged between a top side electrode and a bottom side electrode, with a functionalization material (or at least one functionalization material) arranged over the top side electrode, and with at least one patterned enhanced surface area element arranged between a lower surface of the top side electrode and the functionalization material. The at least one patterned enhanced surface area element is configured to increase non-planarity of the functionalization material, thereby providing a three-dimensional structure configured to increase sensor surface area and reduce analyte diffusion distance to improve sensor performance by enabling capture of an increased amount of analyte. In certain embodiments, at least one patterned enhanced surface area element may promote passive mixing of analyte-containing fluid flowing over such element(s). One or more layers (e.g., a hermeticity layer, an interface layer, and/or a self-assembled monolayer) may be arranged between the top side electrode and the functionalization material. In certain embodiments, one or more patterned enhanced surface area elements may be embodied in: a patterned top side electrode, a patterned photoimageable material, or another patterned layer (e.g., a hermeticity layer or an interface layer) arranged between the top side electrode and the functionalization material. Further provided are fluidic devices incorporating MEMS resonator devices disclosed herein, as well as methods for biological and chemical sensing, and methods for forming MEMS resonator devices and fluidic devices.

In certain embodiments, substantially an entire upper surface of a top side electrode coincident with an active region of a MEMS resonator device comprises a patterned area embodying at least one patterned enhanced surface area element. In other embodiments, less than an entire upper surface of a top side electrode coincident with an active region of a MEMS resonator device is patterned. In certain embodiments, patterning results in formation of a plurality of features having predetermined (e.g., regular) spacing and/or dimensions, as opposed to unintentional defects that would be expected to be random in size and shape. In certain embodiments, defining at least one patterned enhanced surface area element comprises removing material over or from the top side electrode via a subtractive material removal process. For example, wet etching and/or dry etching may be used in conjunction with photolithography to define features of desirable resolution in certain embodiments. In certain embodiments, the defining of at least one patterned enhanced surface area element comprises addition of material over or to the top side electrode via an additive manufacturing process. For example, one or more liftoff deposition processes and/or three dimensional printing may be used.

In certain embodiments, a peripheral boundary of an active region defines a two-dimensional area; and the at least one functionalization material is arranged over the at least one patterned enhanced surface area element over a surface area that is at least 10% greater (or at least 20% greater, or at least 30% greater, or in a range of from 20% greater to 100% greater, or in a range of from 20% greater to 200% greater, or a range of from 20% to 300% greater) than the two-dimensional area. In this manner, the presence of the at least one patterned enhanced surface area element increases the amount of functionalization material available to interact with analyte. In certain embodiments, at least one patterned enhanced surface area element comprises a height or depth that differs from a nominal thickness of the top side electrode by at least 30%, at least 50%, or at least 100%. In certain embodiments, at least one patterned enhanced surface area element includes an undulating height, such as may include at least two, at least three, at least four, at least five, at least ten, or at least twenty transitions between at least one maximum height region and at least one minimum height region.

In certain embodiments, the at least one patterned enhanced surface area element comprises a rigid material, such as a metal, a dielectric material, or the like. Exemplary materials include tungsten or silicon oxide, but other materials may be used. In one example, the at least one patterned enhanced surface area element comprises tungsten or another metal deposited over a top side electrode (which may include aluminum, aluminum alloy, or another suitable metal or combination of metals). In certain embodiments, the deposited metal is compositionally different from a composition of the top side electrode. Tungsten or another metal may be deposited via physical vapor deposition or other sputtering techniques, and/or may be patterned via reactive ion etching (RIE) in a suitable gas environment (e.g., sulfur hexafluoride [$SF_6$] in the case of tungsten), or may be patterned via other means. In another example, the at least one patterned enhanced surface area element comprises silicon oxide [$SiO_2$], silicon nitride [SiN], aluminum nitride [AlN], aluminum oxide [$Al_2O_3$] or another dielectric material, which may be deposited over the top side electrode (which may include gold or another noble metal, aluminum, aluminum alloy, or another suitable metal or combination of metals) via chemical vapor deposition (CVD) or another suitable process. In certain embodiments, silicon oxide [$SiO_2$] or another suitable dielectric material may be selectively etched via RIE or wet etching to define features therein. In further embodiments, the top side electrode may be deposited with excess thickness, and then processed via RIE or wet etching (or another subtractive removal process) to yield the at least one patterned enhanced surface area element.

In other embodiments, the at least one patterned enhanced surface area element may comprise semi-rigid photoimageable materials such as photoresist, SU-8, TBBF, epoxy, solder masks, dielectrics, or the like. Such materials may be used to yield protrusions (e.g., pillars) that are taller and embody a higher aspect (e.g., height/width) ratio than rigid materials. For example, in certain embodiments, the at least one patterned enhanced surface area element may comprise a height/width aspect ratio of at least 2, at least 5, or at least 10, such as protrusions having heights in a range of from 5-20 microns and a width of from 2 to 5 (or 2 to 10) microns. Other dimensional ranges may be used.

In certain embodiments, the at least one patterned enhanced surface area element overlying the top side electrode comprises a density that is greater than that of the top side electrode. In other embodiments, the at least one patterned enhanced surface area element overlying the top side electrode comprises a density that is less than that of the top side electrode.

In certain embodiments, the at least one patterned enhanced surface area element overlying the top side electrode comprises an electrically conductive material in conductive electrical contact with the top side electrode. In other embodiments, the at least one patterned enhanced surface area element overlying the top side electrode comprises an insulating (e.g., dielectric) material.

In certain embodiments, the at least one patterned enhanced surface area element includes grooves or recesses extending through only a portion of a thickness of the top side electrode. In other embodiments, one or more grooves or recesses may extend through an entire thickness of the top side electrode, but the one or more grooves or recesses are configured so as not to interrupt electrical connection to the remainder of the top side electrode (e.g., by avoiding "islands" of electrode material that are electrically isolated from the remainder of the top side electrode).

In certain embodiments, a BAW resonator structure comprises a hexagonal crystal structure piezoelectric material (e.g., aluminum nitride or zinc oxide) that includes a c-axis having an orientation distribution that is non-parallel (and also non-perpendicular) to normal of a face of a substrate over which the piezoelectric material is formed, providing a quasi-shear mode acoustic resonator. Such a c-axis orientation distribution enables creation of shear displacements at certain frequencies (which beneficially enables operation of a BAW resonator-based sensing device in liquid environments), and enables creation of longitudinal displacements at other frequencies (which may be useful to promote localized mixing). Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric material having an inclined c-axis orientation are disclosed in U.S. Pat. No. 4,640,756 issued on Feb. 3, 1987, with the foregoing patent hereby being incorporated by reference herein.

Before describing devices incorporating patterned enhanced surface area elements and methods for fabricating such elements, exemplary bulk acoustic wave MEMS resonator devices, associated layers useful for providing biochemical sensing utility, and fluidic devices incorporating MEMS resonator devices will be introduced.

Micro-electrical-mechanical system (MEMS) resonator devices according to certain embodiments include a substrate, a BAW resonator structure arranged over at least a portion of the substrate, and a functionalization material arranged over at least a portion of an active region of the BAW resonator structure. Various layers may be arranged between the functionalization material and a top side electrode (which is coincident with the active region of the BAW resonator structure), such as: a hermeticity layer (e.g., to protect the top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material. In certain embodiments, multiple functionalization materials may be provided.

FIG. 1 is a schematic cross-sectional view of a portion of a bulk acoustic wave MEMS resonator device 10 useable with embodiments disclosed herein. The resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, the acoustic reflector 14 includes alternating thin layers 16, 18 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

In certain embodiments, the piezoelectric material 22 comprises a hexagonal crystal structure piezoelectric material (e.g., aluminum nitride or zinc oxide) that includes a c-axis having an orientation distribution that is predominantly non-parallel to (and may also be non-perpendicular to) normal of a face of the substrate 12. Under appropriate conditions, presence of a c-axis having an orientation distribution that is predominantly non-parallel to normal of a face of a substrate enables a BAW resonator structure to be configured to exhibit a dominant shear response upon application of an alternating current signal across a top side electrode and a bottom side electrode.

The bulk acoustic wave MEMS resonator device 10 shown in FIG. 1 lacks any layers (e.g., including functionalization material) overlying the active region 30 that would permit the resonator device 10 to be used as a biochemical sensor. If desired, at least portions of the resonator device 10 shown in FIG. 1 (e.g., including the active region 30) may be overlaid with various layers, such as one or more of: a hermeticity layer, an interface layer, a self-assembled monolayer (SAM), and/or a functionalization material (which may include specific binding material or non-specific binding material).

Figure 2:
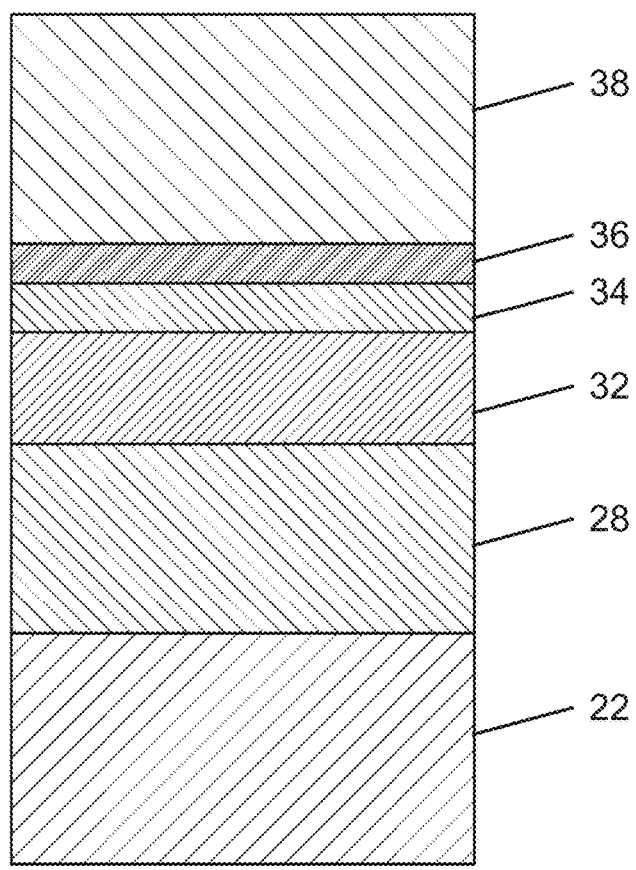
FIG. 2 is a schematic cross-sectional view of an upper portion of a BAW MEMS resonator device including a piezoelectric material and a top side electrode overlaid with a hermeticity layer, an interface layer, a self-assembled monolayer, and a functionalization (e.g., specific binding) material.

FIG. 2 is a schematic cross-sectional view of an upper portion of a BAW MEMS resonator device including a piezoelectric material 22 and a top side electrode 28 overlaid with a hermeticity layer 32, an interface layer 34, a self-assembled monolayer (SAM) 36, and a functionalization (e.g., specific binding) material 38. In certain embodiments, one or more blocking materials (not shown) may be applied during fabrication, such as over portions of the interface layer 34 to prevent localized attachment of one or more subsequently deposited layers, or (if applied over selected regions of the SAM 36 or functionalization material 38) to prevent analyte capture in regions not overlying the active region 30 of the BAW MEMS resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., by using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide [$SiO_2$]. Alternative materials incorporating hydroxylated oxide surfaces for forming interface layers include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 $g/m^2/day$). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 $g/m^2/day$) according to certain embodiments. In certain embodiments, a hermeticity layer includes at least one of aluminum oxide ($Al_2O_3$) or silicon nitride (SiN). In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an S—H head group, a tail group, and a backbone comprising an alkyl chain. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, specific binding materials may be applied on or over a SAM using a microarray spotting needle or other suitable methods. In certain embodiments, an interface layer may be patterned (e.g., using photolithography for defining the interface layer) with a high dimensional tolerance over only a portion of a BAW resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active areas of a multi-resonator structure (i.e., one or more resonator structures including multiple active regions), optionally in combination with one or more active areas that are devoid of specific binding materials to serve as comparison (or "reference") regions. In certain embodiments, a functionalization (e.g., bio-functionalization) material may provide non-specific binding utility.

Certain embodiments are directed to a fluidic device including multiple bulk acoustic wave MEMS resonator structures as disclosed herein and including a fluidic passage (e.g., a channel, a chamber, or the like) arranged to conduct a liquid to contact at least one functionalization (e.g., specific binding) material arranged over at least one active region of the BAW MEMS resonator structures. Such a device may be microfluidic in scale, and may comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a SAM over portions thereof (optionally preceded by deposition of a hermeticity layer and an interface layer), a microfluidic device may be fabricated by forming one or more walls defining lateral boundaries of a microfluidic passage over a first bulk acoustic wave MEMS resonator structure with an active region thereof arranged along a bottom surface of the microfluidic passage, and then enclosing the microfluidic passage using a cover or cap layer that may define fluidic ports (e.g., openings) enabling fluid communication with the microfluidic passage. In certain embodiments, functionalization (e.g., specific binding) material may be pre-applied to the active region of a bulk acoustic wave MEMS resonator structure before formation of the microfluidic passage; in other embodiments, functionalization material may be applied over an active region of a bulk acoustic wave resonator structure following formation of the microfluidic passage.

Walls of a microfluidic passage may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM, functionalization material, and/or blocking layers, with an SU-8 negative epoxy resist or other photoimageable material. In certain embodiments, a cover or cap layer may be integrally formed with one or more walls (e.g., via molding or another suitable process) to define a portion of an upper boundary as well as lateral boundaries of at least one fluidic passage, and the integrally formed partial cover/wall structure may be applied (e.g., adhered or otherwise bonded) over at least a portion of a bulk acoustic wave resonator structure to enclose the at least one fluidic passage.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO)-containing materials. An ideal blocking buffer would bind to all potential sites of non-specific interaction away from an active region. To optimize a blocking buffer for a particular analysis, empirical testing may be used to determine signal-to-noise ratio. No single chemical or biological blocking material is ideal for every situation, since each antibody-antigen pair has unique characteristics.

Figure 3:
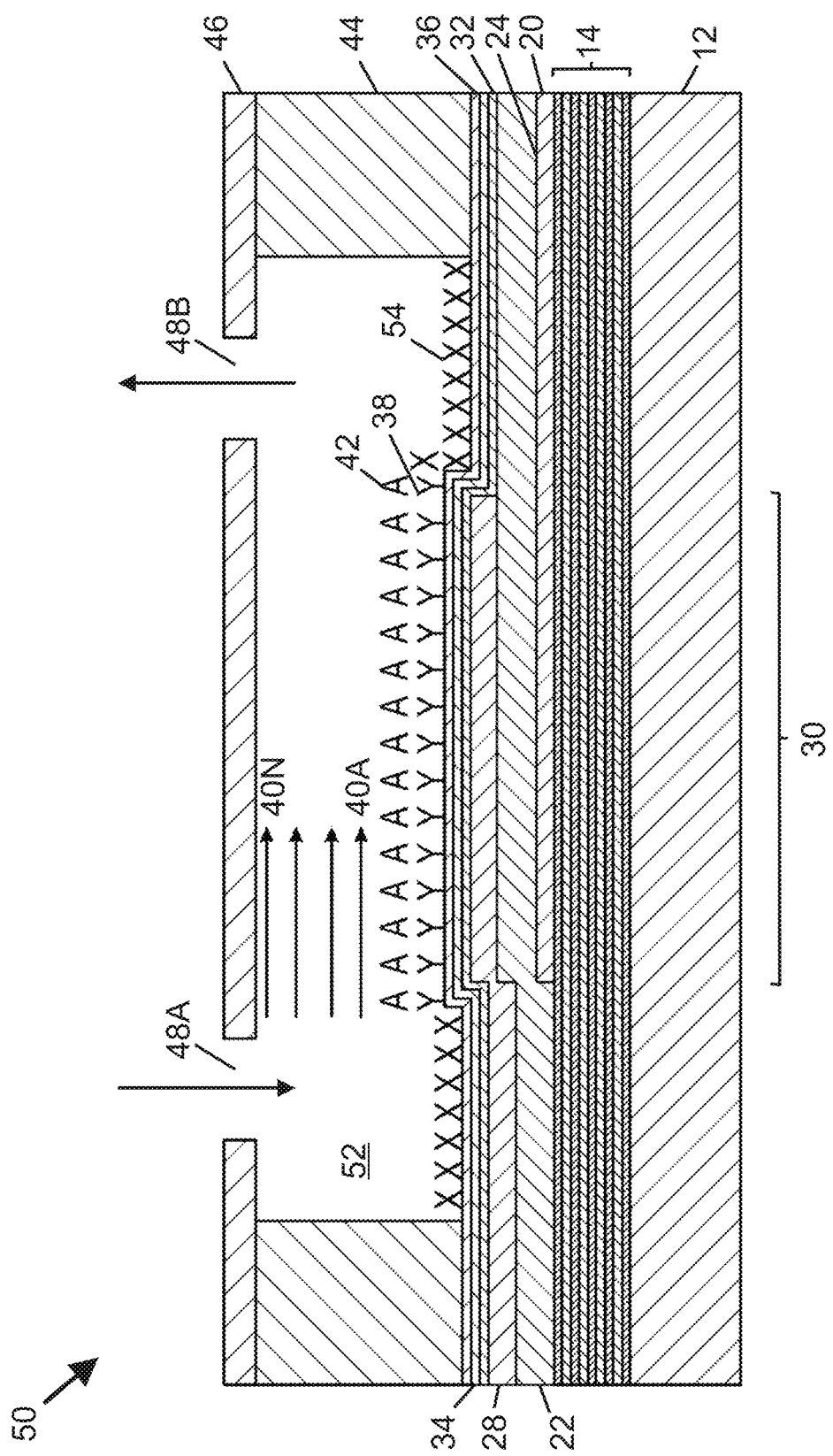
FIG. 3 is a schematic cross-sectional view of a portion of a fluidic device (e.g., a biochemical sensor device) including a fluidic passage bounded from below by a BAW resonator structure, bounded laterally by walls, and bounded from above by a cover or cap layer defining fluidic ports, with a self-assembled monolayer (SAM) arranged over the entire piezoelectric material and blocking material arranged over portions of the SAM non-coincident with an active region, to serve as a first comparison device intended to provide context for subsequently described embodiments of the disclosure.

FIG. 3 is a schematic cross-sectional view of a portion of a fluidic device 50 (e.g., a biochemical sensor device) including a fluidic passage 52 (which may be microfluidic in character) that is bounded from below by a bulk acoustic wave resonator structure including an active region 30, bounded laterally by walls 44, and bounded from above by a cover or cap layer 46 defining upper surface fluidic ports 48A, 48B, with the fluidic device 50 serving as a first comparison device intended to provide context for subsequently described embodiments of the disclosure. The fluidic device 50 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. The bottom side electrode 20 is arranged along a portion of a lower surface 24 of the piezoelectric material 22. The top side electrode 28 and the piezoelectric material 22 are overlaid with a hermeticity layer 32, an interface layer 34, and a self-assembled monolayer (SAM) 36. Portions of the SAM 36 between the active region 30 and the walls 44 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte. Walls 44 that are laterally displaced from the active region 30 extend upward from the chemical or biological blocking material 54 to define lateral boundaries of the fluidic passage 52 containing the active region 30. The walls 44 may be formed of any suitable material, such as a laser-cut "stencil" layer of thin polymeric materials and/or laminate materials, optionally including one or more self-adhesive surfaces (e.g. adhesive tape). Optionally such walls 44 may be formed prior to deposition of the SAM 36, functionalization material 38, and chemical or biological blocking material 54 with an SU-8 negative epoxy resist or other photoimageable material. The cover or cap layer 46 defining upper surface fluidic ports 48A, 48B is further provided to provide an upper boundary for the fluidic passage 52. The cover or cap layer 46 may be formed by defining ports (e.g., via laser cutting or water jet cutting) in a layer of an appropriate material (e.g., a substantially inert polymer, glass, silicon, ceramic, or the like), and adhering the cover or cap layer 46 to top surfaces of the walls 44.

In use of the fluidic device 50, a fluid sample may be supplied through the first fluidic port 48A into the fluidic passage 52 over the active region 30 and through the second fluidic port 48B to exit the fluidic passage 52. Due to the laminar nature of the fluid flow within the fluidic passage 52, the fluid volume may be modeled and behave as a "stack" of horizontal fluid layers including a lowermost fluid layer 40A and an uppermost fluid layer 40N. An analyte 42 contained in the lowermost fluid layer 40A of the fluid sample will tend to bind with functionalization material 38 arranged over the active region 30. Analyte contained in fluid layers above the lowermost fluid layer 40A (including the uppermost fluid layer 40N) may not be available to bind with the functionalization material 38, since diffusion of analyte (e.g., in a vertical direction) between the fluid layers 40A-40N may occur slowly. Assuming that sufficient analyte is present proximate to the lowermost fluid layer 40A to bind with functionalization material 38 arranged over the active region 30, when a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude magnitude property, a frequency property, or a phase property, such as a shift in resonant frequency) of the BAW resonator structure may be detected to indicate a presence and/or quantity of analyte bound to the functionalization material 38.

Figure 4:
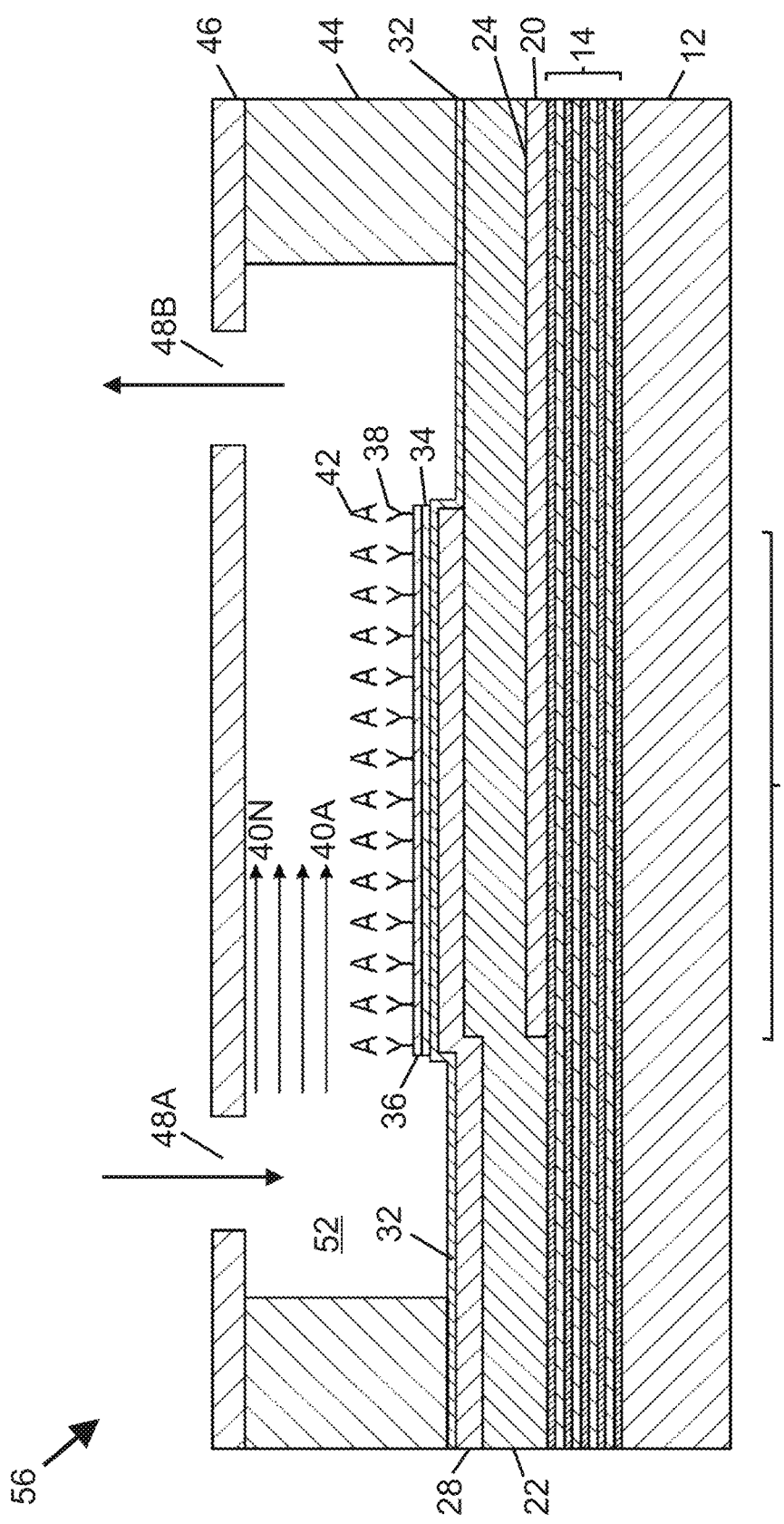
FIG. 4 is a schematic cross-sectional view of a portion of a fluidic device (e.g., a biochemical sensor device) including a fluidic passage bounded from below by a BAW resonator structure, bounded laterally by walls, and bounded from above by a cover or cap layer defining fluidic ports, with a SAM and functionalization material arranged only over an active region, to serve as a second comparison device intended to provide context for subsequently described embodiments of the disclosure.

FIG. 4 is a schematic cross-sectional view of a portion of a fluidic device (e.g., a biochemical sensor device) 56 similar to the fluidic device 50 of FIG. 3, serving as a second comparison device intended to provide context for subsequently described embodiments of the disclosure. As compared to the fluidic device 50 of FIG. 3, the fluidic device 56 of FIG. 4 includes an interface layer 34 and a SAM 36 that are provided solely over an active region 30 instead of over an entirety of piezoelectric material 22. Such configuration may be provided by controlling lateral boundaries of the interface layer 34 (e.g., by photolithographic patterning and selective etching, for example). The fluidic device 56 includes a fluidic passage 52 that is bounded from below by a bulk acoustic wave MEMS resonator structure including the active region 30, bounded laterally by walls 44, and bounded from above by a cover or cap layer 46 defining upper surface fluidic ports 48A, 48B. The fluidic device 56 includes a substrate 12 overlaid with an acoustic reflector 14, and a bottom side electrode 20 arranged generally below the piezoelectric material 22. The bottom side electrode 20 is arranged along a portion of a lower surface 24 of the piezoelectric material 22. The top side electrode 28 extends over a portion of the piezoelectric material 22, wherein a portion of the piezoelectric material 22 arranged between the top side electrode 28 and the bottom side electrode 20 embodies the active region 30 of the BAW MEMS resonator structure. A hermeticity layer 32 is arranged over the top side electrode 28 and the piezoelectric material 22. The interface layer 34 and the SAM 36 are provided over a portion of the hermeticity layer 32 that is registered with the active region 30. The SAM 36 is overlaid with a layer of functionalization (e.g., specific binding) material 38 arranged to bind at least one analyte (e.g., analyte 42). Walls 44 that are laterally displaced from the active region 30 extend upward from the hermeticity layer 32 to define lateral boundaries of the fluidic passage 52 containing the active region 30. The cover or cap layer 46 defining upper surface fluidic ports 48A, 48B is provided over the walls 44 to provide an upper boundary for the fluidic passage 52. Operation of the fluidic device 56 of FIG. 4 is similar to the operation of the fluidic device 50 of FIG. 3. A volume of fluid may behave as a "stack" of horizontal fluid layers including a lowermost fluid layer 40A and an uppermost fluid layer 40N within the fluidic passage 52, wherein the lowermost fluid layer 40A is proximate to functionalization material 38 overlying the active region 30. Assuming the presence of sufficient analyte in the fluid (including the lowermost fluid layer 40A) when a bulk acoustic wave having a dominant shear component is induced in the active region 30 by supplying an electrical (e.g., alternating current) signal of a desired frequency to the bottom and top side electrodes 20, 28, then a change in electroacoustic response of the BAW resonator structure may be detected to indicate a presence and/or quantity of analyte bound to the functionalization material 38.

FIG. 5A is a schematic cross-sectional view of a portion of a BAW MEMS resonator device 10A similar to the resonator device 10 of FIG. 1, but including a top side electrode 58 embodying a patterned enhanced surface area element with multiple upwardly extending protrusions 60 separated by grooves or recesses 62, with the upwardly extending protrusions 60 and grooves or recesses 62 arranged over an active area 30. A piezoelectric material 22 is arranged between the top side electrode 58 and a bottom side electrode 20, wherein an area in which the piezoelectric material 22 is arranged between overlapping portions of the top side electrode 58 and the bottom side electrode 20 defines the active region 30. The BAW MEMS resonator device 10A further includes a substrate 12 (e.g., silicon or another semiconductor material) and acoustic reflector 14 arranged over the substrate 12, wherein the bottom side electrode 20 and the piezoelectric material 22 are arranged over the acoustic reflector 14. As shown in FIG. 5A, the upwardly extending protrusions 60 embody continuous extensions of the top side electrode 58, such as may be formed by a subtractive manufacturing or removal process (e.g., etching) starting with a thick electrode, or such as may be formed by an additive manufacturing process (e.g., liftoff).

FIG. 5B is a schematic cross-sectional view of the BAW MEMS resonator device portion 10A of FIG. 5A following formation of a hermeticity layer 32 and an interface layer 34 over the top side electrode 58 and over the piezoelectric material 22. The hermeticity layer 32 may serve to protect the top side electrode 58 (which may comprise a reactive material such as aluminum or aluminum alloy) from attack in a corrosive liquid environment, and the interface layer 34 may serve to facilitate chemical binding of a SAM (not shown) arranged to receive at least one functionalization material.

Figure 6A:
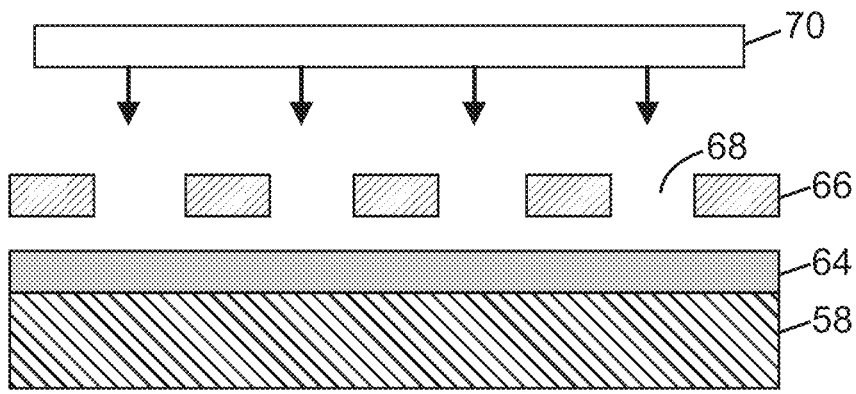
FIGS. 6A-6E provide schematic cross-sectional views of a portion of a top side electrode with recesses in various states of formation in an upper surface thereof.
Figure 6B:
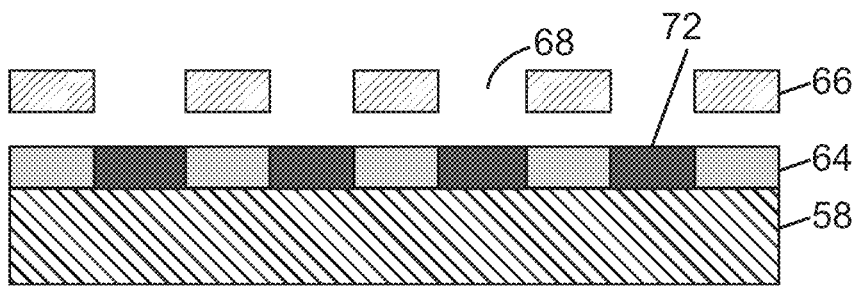
Figure 6C:
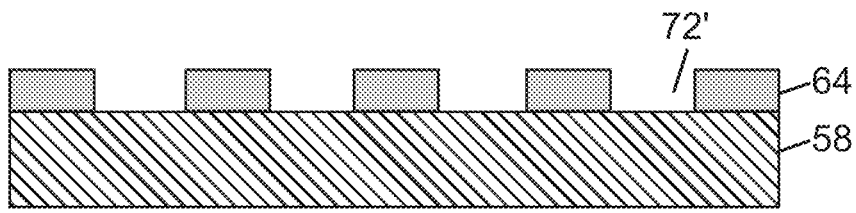
Figure 6D:
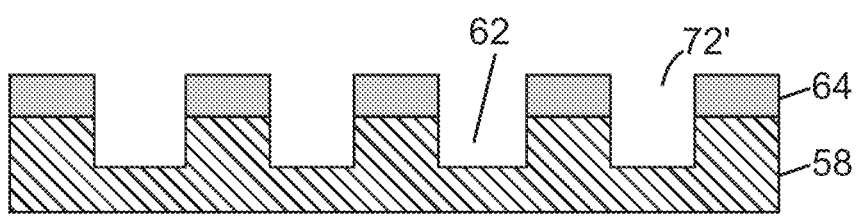
Figure 6E:
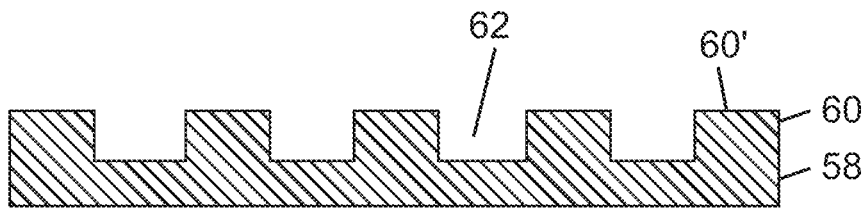
Figure 7A:
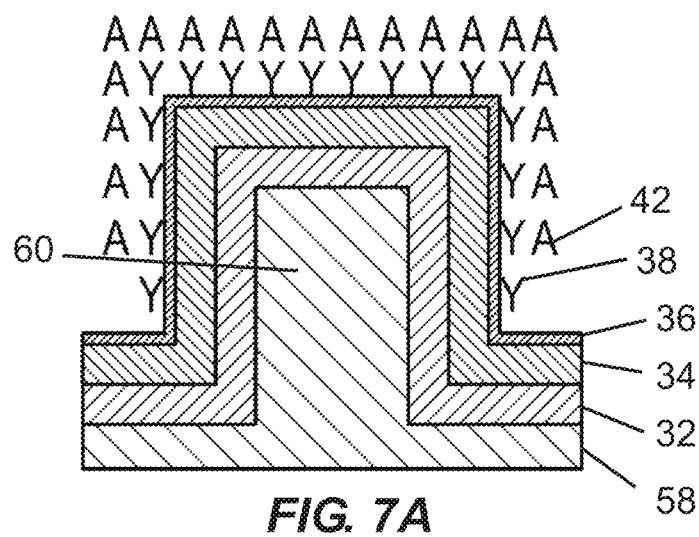
FIG. 7A is a schematic cross-sectional view of a single protrusion of a patterned enhanced surface area element including an upwardly extending portion of a top side electrode, with the protrusion being overlaid with a hermeticity layer, an interface layer, a self-assembled monolayer, and a functionalization material with analyte bound thereto, according to one embodiment.

FIGS. 6A-6E provide schematic cross-sectional views of a portion of a top side electrode 58 of a bulk acoustic wave resonator structure, with recesses in various states of formation in an upper surface of the top side electrode 58 using a process such as photolithographic patterning and etching. FIG. 6A illustrates the top side electrode 58 overlaid with a layer of photoresist 64, with a photomask 66 defining mask windows 68 arranged between the layer of photoresist 64 and an electromagnetic (e.g., ultraviolet) radiation source 70. FIG. 6B illustrates the photomask 66, top side electrode 58, and layer of photororesist 64 following impingement of radiation through the mask windows 68 to form soluble regions 72 in the layer of photoresist 64. Such soluble regions 72 may be removed by application of a suitable developer chemical to yield a layer of photoresist 64 defining photoresist windows 72', as shown in FIG. 6C. Thereafter, a suitable etchant may be applied through the photoresist windows 72' to form grooves or recesses 62 in the top side electrode 58, as shown in FIG. 6D. Finally, the layer of photoresist 64 may be removed to yield a top side electrode 58 including an exposed upper surface 60' (which may correspond to an upward protrusion 60) and grooves or recesses 62 that extend from the upper surface 60' into an interior of the top side electrode 58 between respective upward protrusions 60, as shown in FIG. 6E. The resulting upwardly extending protrusions 60 and grooves or recesses 62 may be used to promote fluid movement and mixing when exposed to moving flow of analyte-containing fluid, by causing undulating movement of fluid over and/or past the grooves or recesses 62. Although FIG. 6E shows the grooves or recesses 62 as extending through only a portion of a thickness of the top side electrode 58, in certain embodiments, one or more grooves or recesses 62 may extend through the entire thickness of the top side electrode 58, provided that the one or more grooves or recesses 62 may preferably be configured so as not to interrupt electrical connection to the remainder of the top side electrode 58. The resulting top side electrode 58 including upwardly extending protrusions 60 and grooves or recesses 62 may be considered a patterned enhanced surface area element. Upon application of a functionalization material over the top side electrode 58 (such as shown in FIG. 7A), the upwardly extending protrusions 60 and grooves or recesses 62 provide a three-dimensional structure configured to increase sensor surface area relative to a top side electrode having the same footprint but with a substantially planar upper surface. Such increased surface area enables improved sensor performance by enabling capture of an increased amount of analyte, and the patterned enhanced surface area element may also promote passive mixing of analyte-containing fluid flowing over the top side electrode 58. The grooves or recesses 62 may be arranged to bound a portion of a fluidic passage (e.g., a channel). In certain embodiments, various grooves or recesses 62 are laterally displaced and/or non-intersecting relative to one another.

FIG. 7A is a schematic cross-sectional view of a single protrusion 60 of a patterned enhanced surface area element embodying an upwardly extending portion of a top side electrode 58, with the protrusion 60 being overlaid with a hermeticity layer 32, an interface layer 34, a self-assembled monolayer 36, and a functionalization material 38 with analyte 42 bound thereto, according to one embodiment. In certain embodiments, the protrusion 60 may be formed by photolithographic patterning and selective etching as described herein. Such process may comprise a subtractive material removal process. In other embodiments, the protrusion 60 may be formed using a lift-off process, whereby photoresist material is applied over a surface of a top side electrode, windows are defined in the photoresist material, material is deposited through the windows to contact and adhere to the top side electrode, and the photoresist material is subsequently removed. In certain embodiments, the deposited material comprises a metal or other conductive material (optionally having the same composition as the top side electrode), and may be applied via sputtering or another suitable material addition process.

Figure 7B:
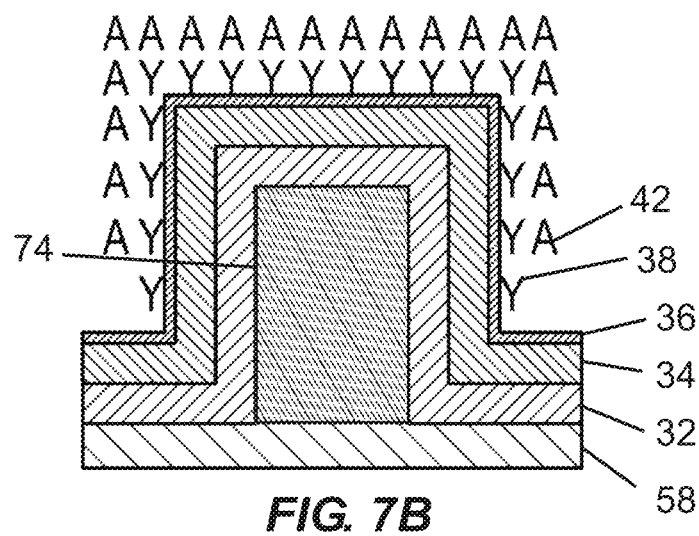
FIG. 7B is a schematic cross-sectional view of a single protrusion of a patterned enhanced surface area element embodied in a deposited material (e.g., photoimageable material) extending upward from a surface of a top side electrode, with the protrusion being overlaid with a hermeticity layer, an interface layer, a self-assembled monolayer, and a functionalization material with analyte bound thereto, according to one embodiment.

FIG. 7B is a schematic cross-sectional view of a single protrusion 74 of a patterned enhanced surface area element embodied in a deposited material extending upward from a surface of a top side electrode 58, with the protrusion 74 being overlaid with a hermeticity layer 32, an interface layer 34, a self-assembled monolayer 36, and a functionalization material 38 with analyte 42 bound thereto, according to one embodiment. In certain embodiments, the deposited material forming the protrusion 74 comprises photoimageable material that is selectively patterned using a photomask and an electromagnetic (e.g., ultraviolet) radiation source, which may be embodied in a coherent (e.g., laser) or non-coherent source. In other embodiments, the deposited material forming the protrusion 74 may be deposited via another material addition process, such as three-dimensional printing. Following addition of the deposited material forming the protrusion 74 over the top side electrode 58, the remaining layers 32, 34, 36, 38 may be formed over the protrusion 74 and the top side electrode 58 as described previously herein.

Figure 8:
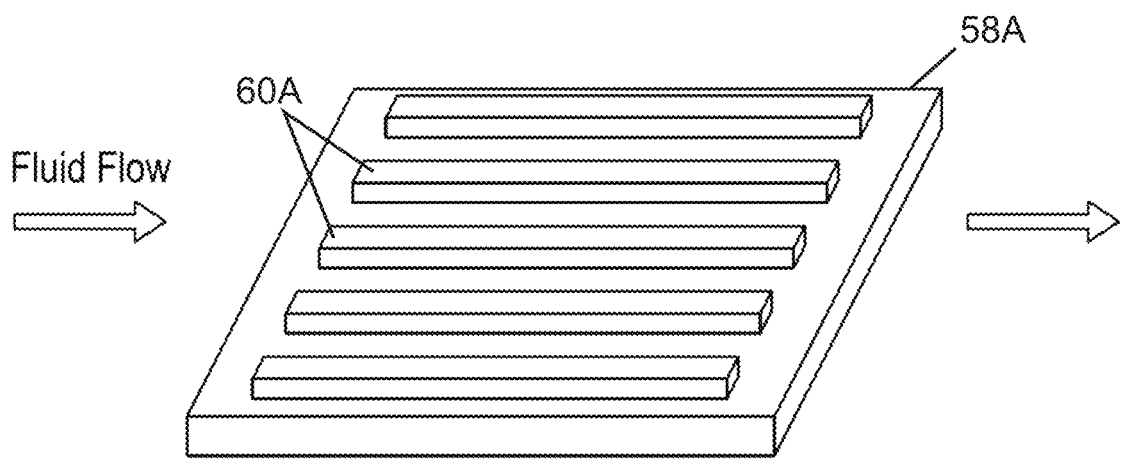
FIG. 8 is a schematic perspective view of an exemplary top side electrode suitable for use with a bulk acoustic wave MEMS resonator device as described herein, with the top side electrode embodying a patterned enhanced surface area element including a plurality of upwardly protruding, elongated parallel rectangular protrusions, according to one embodiment.

FIG. 8 is a schematic perspective view of an exemplary top side electrode 58A suitable for use with a bulk acoustic wave MEMS resonator device as described herein, with the top side electrode 58A embodying a patterned enhanced surface area element including a plurality of upwardly protruding, elongated parallel rectangular protrusions 60A according to one embodiment. In certain embodiments, the rectangular protrusions 60A may be oriented in parallel with a direction of fluid flow, as shown in FIG. 8. In other embodiments, rectangular protrusions may be oriented perpendicular to, or at an angle between 0 to 90 degrees relative to, a direction of fluid flow over a top side electrode.

Figure 9A:
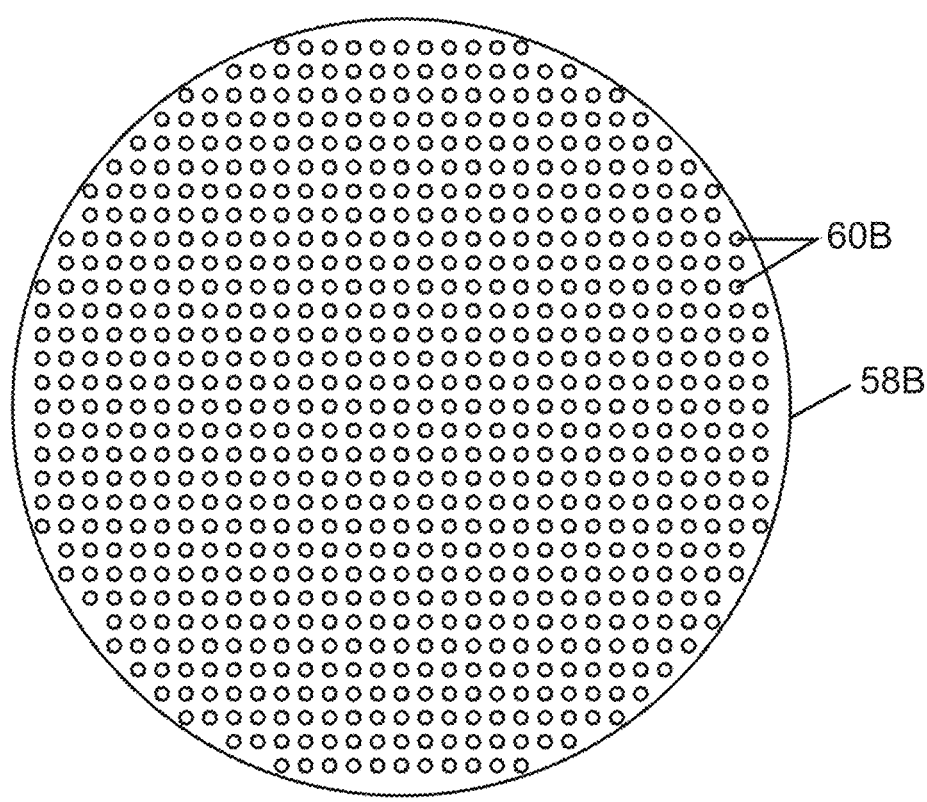
FIG. 9A is a schematic top plan view of an exemplary top side electrode suitable for use with a bulk acoustic wave MEMS resonator device as described herein, with the top side electrode embodying a patterned enhanced surface area element including a plurality of upwardly protruding portions configured as cylindrical posts, according to one embodiment.
Figure 9B:
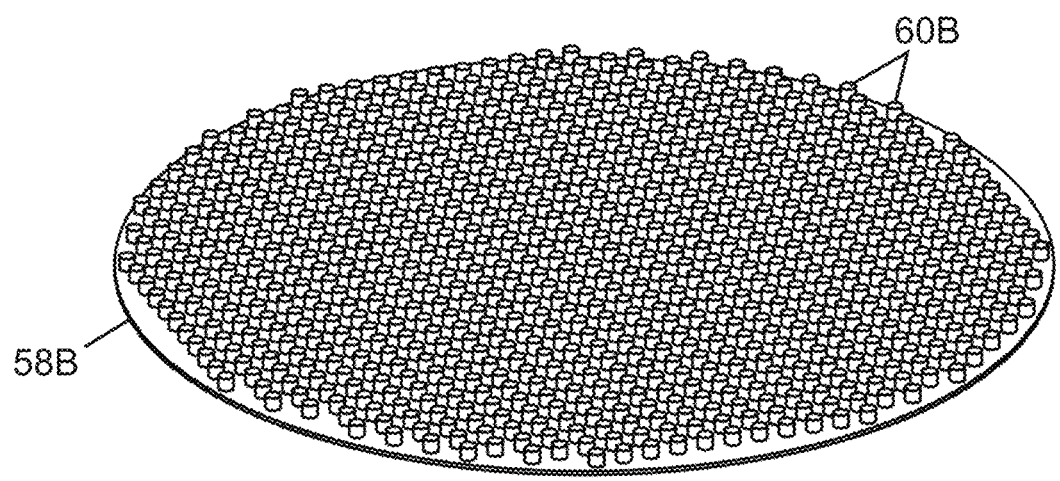
FIG. 9B is a perspective view of the top side electrode of FIG. 9A.

FIGS. 9A and 9B illustrate an exemplary top side electrode 58B suitable for use with a bulk acoustic wave MEMS resonator device as described herein, with the top side electrode 58B embodying a patterned enhanced surface area element including a plurality of upwardly extending protrusions 60B configured as cylindrical posts, according to one embodiment. In certain embodiments, the protrusions 60B may be formed via a subtractive manufacturing process (e.g., photolithographic patterning and etching). In certain embodiments, the protrusions 60B may be formed via an additive manufacturing process (e.g., liftoff and/or three-dimensional printing). As shown in FIGS. 9A and 9B, the protrusions 60B may be arranged in a grid. Although more than 400 protrusions are shown in FIGS. 9A and 9B, any suitable number of protrusions and/or recesses may be provided with patterned enhanced surface area elements according to certain embodiments.

FIG. 10A is a schematic cross-sectional view of a portion of a bulk acoustic wave (BAW) resonator structure 10B according to one embodiment. The BAW resonator structure 10B includes a substrate 12, an acoustic reflector 14 arranged over the substrate 12, a piezoelectric material 22, and bottom and top side electrodes 20, 58. The bottom side electrode 20 is arranged along a portion of a lower surface of the piezoelectric material 22 (between the acoustic reflector 14 and the piezoelectric material 22), and the top side electrode 58 is arranged along a portion of an upper surface of the piezoelectric material 22. An area in which the piezoelectric material 22 is arranged between overlapping portions of the top side electrode 58 and the bottom side electrode 20 is considered an active region 30 of the resonator structure 10B. The top side electrode 58 embodies a patterned enhanced surface area element registered with the active region 30, with the patterned enhanced surface area element including a plurality of grooves or recesses 62 defined in the top side electrode 58. Although the grooves or recesses 62 are illustrated as extending through an entire thickness of the top side electrode 58, the grooves or recesses 62 are preferably configured to avoid "islands" of electrode material that are electrically isolated from other portions of the top side electrode 58, so as not to interrupt electrical connection to the remainder of the top side electrode 58. In certain embodiments, the grooves or recesses 62 may be formed by a subtractive manufacturing process such as photolithographic patterning and selective etching, and/or by other method steps disclosed herein.

FIG. 10B is a schematic cross-sectional view of the portion of a BAW resonator structure 10B of FIG. 10A following formation of multiple layers (e.g., a hermeticity layer 32 and an interface layer 34) over the piezoelectric material 22 and the top side electrode 58, to overlie the active region 30. The interface layer 34 may also be overlaid with a SAM and at least one functionalization material (not shown). The presence of grooves or recesses 62 in the top side electrode 58 over the active region 30 forms at least one patterned enhanced surface area element that serves to increase surface area of any functionalization material overlying the active region 30. Preferably, at least the portion of the interface layer 34 overlying the active region 30 is overlaid with a SAM and at least one functionalization material (not shown).

Figure 10C:
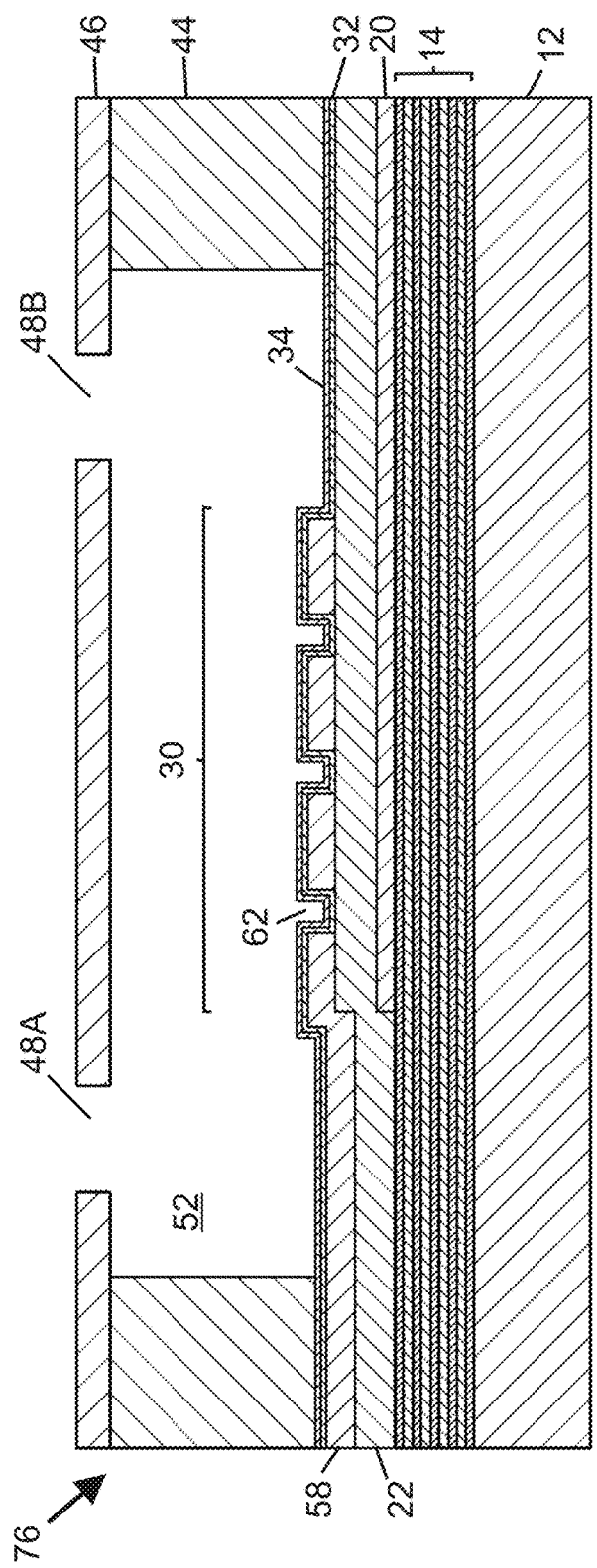
FIG. 10C is a schematic cross-sectional view of a portion of a fluidic device (e.g., a biochemical sensor device) including a fluidic passage bounded from below by the BAW resonator structure of FIG. 10B, bounded laterally by walls, and bounded from above by a cover or cap layer defining fluidic ports, according to one embodiment.

FIG. 10C is a schematic cross-sectional view of a portion of a fluidic device 76 (e.g., a biochemical sensor device) including a fluidic passage 52 bounded from below by the BAW resonator structure of FIG. 10B, bounded laterally by walls 44, and bounded from above by a cover or cap layer 46 defining fluidic ports 48A, 48B, according to one embodiment. In use of the fluidic device 76, a fluid sample may be supplied through the first fluidic port 48A into the fluidic passage 52 over the active region 30 and through the second fluidic port 48B to exit the fluidic passage 52. An analyte (not shown) contained in at least a lower portion of the fluid sample within the fluidic passage 52 may bind with functionalization material (not shown) arranged over the active region 30. When a bulk acoustic wave having a dominant shear component is induced in the active region 30 by supplying an electrical (e.g., alternating current) signal of a desired frequency to the bottom and top side electrodes 20, 58, a change in electroacoustic response (e.g., at least one of an amplitude magnitude property, a frequency property, or a phase property, such as a shift in resonant frequency) of the BAW resonator structure may be detected to indicate a presence and/or quantity of analyte bound to the functionalization material.

Figure 11A:
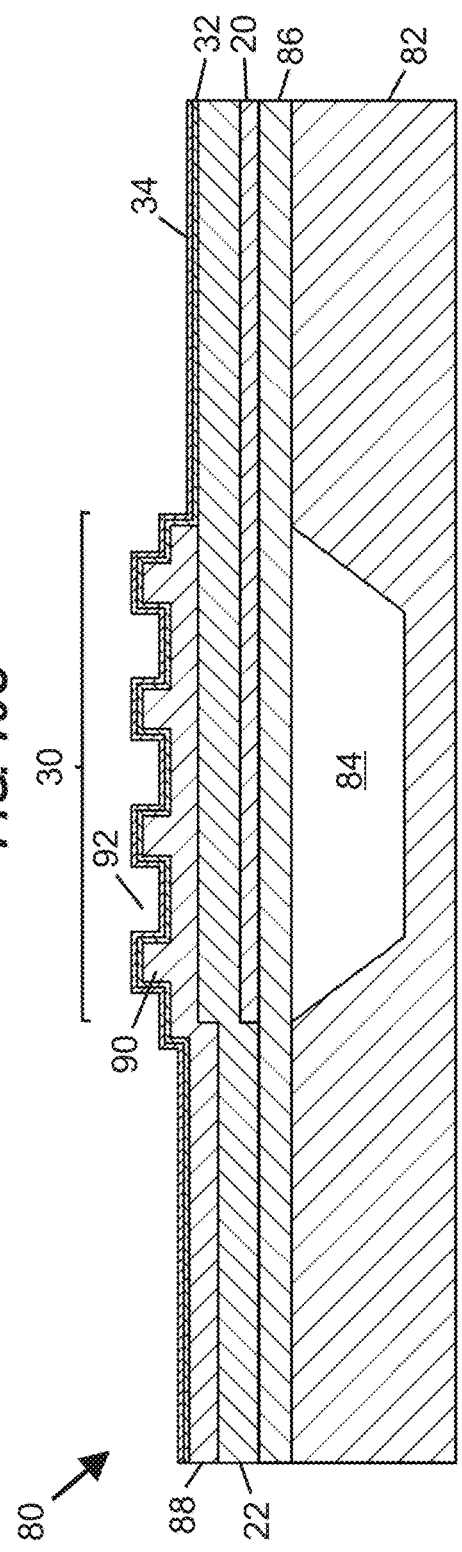
FIG. 11A is a schematic cross-sectional view of a portion of a film bulk acoustic wave resonator (FBAR) structure with a top side electrode embodying at least one patterned enhanced surface area element including a plurality of upwardly extending protrusions that are overlaid with (at least) a hermeticity layer and an interface layer, according to one embodiment.

FIG. 11A is a schematic cross-sectional view of a film bulk acoustic wave resonator (FBAR) structure 80 including an active region 30, with the FBAR structure 80 being overlaid with (at least) a hermeticity layer 32 and an interface layer 34 suitable for receiving at least one functionalization (e.g., specific binding or non-specific binding) material, according to one embodiment. The FBAR structure 80 includes a top side electrode 88 including multiple upwardly extending protrusions 90 that are separated by recesses 92 to form at least one patterned enhanced surface area element registered with the active region 30, with the protrusions 90 and recesses 92 being formable by any methods disclosed herein. The FBAR structure 80 includes a substrate 82 (e.g., silicon or another semiconductor material) defining a cavity 84 that is covered by a support layer 86 (e.g., silicon dioxide). A bottom side electrode 20 is arranged over a portion of the support layer 86, a piezoelectric material 22, preferably embodying inclined c-axis hexagonal crystal structure piezoelectric material (e.g., AlN or ZnO), is arranged over the bottom side electrode 20 and the support layer 86, and the top side electrode 88 is arranged over at least a portion of a top surface of the piezoelectric material 22. A portion of the piezoelectric material 22 arranged between the top side electrode 88 and the bottom side electrode 20 embodies the active region 30 of the FBAR structure 80. The active region 30 is arranged over and registered with the cavity 84 disposed below the support layer 86. The cavity 84 serves to confine acoustic waves induced in the active region 30 by preventing dissipation of acoustic energy into the substrate 82, since acoustic waves do not efficiently propagate across the cavity 84. In this respect, the cavity 84 provides an alternative to the acoustic reflector 14 illustrated in FIGS. 1, 3-5B, and 10A-10C. Although the cavity 84 shown in FIG. 11A is bounded from below by a thinned portion of the substrate 82, in alternative embodiments at least a portion of the cavity 84 may extend through an entire thickness of the substrate 82. Steps for forming the FBAR structure 80 may include defining the cavity 84 in the substrate 82, filling the cavity 84 with a sacrificial material (not shown) optionally followed by planarization of the sacrificial material, depositing the support layer 86 over the substrate 82 and the sacrificial material, removing the sacrificial material (e.g., by flowing an etchant through vertical openings defined in the substrate 82 or the support layer 86, or lateral edges of the substrate 82), depositing the bottom side electrode 20 over the support layer 86, growing (e.g., via sputtering or other appropriate methods) the piezoelectric material 22, and depositing the top side electrode 88.

Figure 11B:
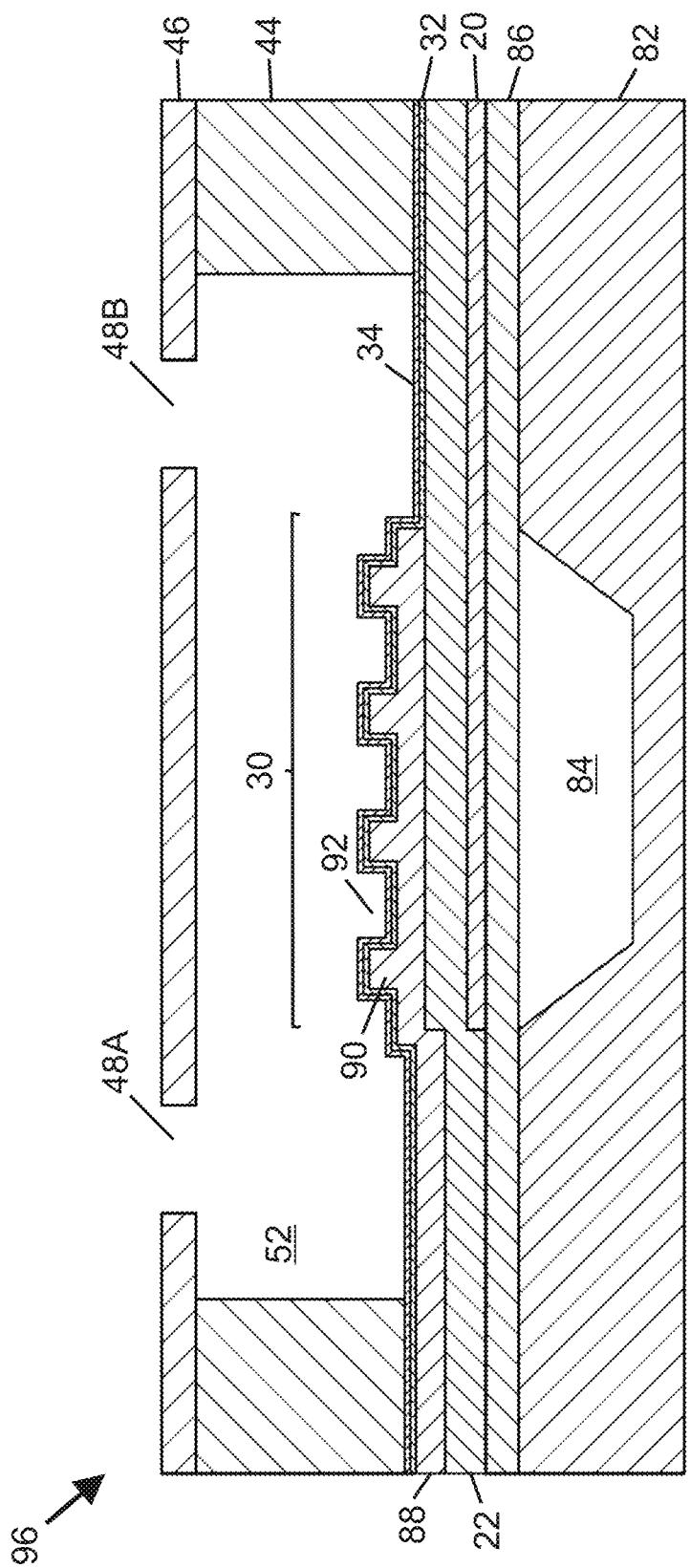
FIG. 11B is a schematic cross-sectional view of a portion of a fluidic device (e.g., a biochemical sensor device) including a fluidic passage bounded from below by the FBAR structure of FIG. 11A, bounded laterally by walls, and bounded from above by a cover or cap layer defining fluidic ports according to one embodiment.

FIG. 11B is a schematic cross-sectional view of a portion of a fluidic device 96 (e.g., a biochemical sensor device) including a fluidic passage 52 bounded from below by the FBAR structure of FIG. 11A, bounded laterally by walls 44, and bounded from above by a cover or cap layer 46 defining upper surface fluidic ports 48A, 48B according to one embodiment. The FBAR structure 80 (shown in FIG. 11A), the walls 44, and the cover or cap layer 46 define a fluidic passage 52 (which may be microfluidic in character) containing the active region 30. Although not shown, functionalization material (optionally overlying a SAM) is preferably arranged over the active region 30, over the interface layer 34. In use of the fluidic device 96, a fluid sample may be supplied through the first fluidic port 48A into the fluidic passage 52 over the active region 30 and through the second fluidic port 48B to exit the fluidic passage 52. If sufficient analyte is present in the fluid sample to bind with functionalization material (not shown) overlying the active region 30, when a bulk acoustic wave having a dominant shear component is induced in the active region 30 by supplying an electrical (e.g., alternating current) signal of a desired frequency to the bottom and top side electrodes 20, 88, a change in electroacoustic response (e.g., at least one of an amplitude magnitude property, a frequency property, or a phase property—such as a shift in resonant frequency) of the BAW resonator structure may be detected to indicate a presence and/or quantity of analyte bound to the functionalization material. Presence of the upwardly extending protrusions 90 and recesses 92 (which form at least one patterned enhanced surface area element) provide increased surface area for functionalization material (thereby increasing sensor surface area and reducing analyte diffusion distance) to improve sensor performance by enabling capture of an increased amount of analyte, and may also promote enhanced mixing of analyte-containing fluid flowing over the at least one patterned enhanced surface area element.

Figure 12:
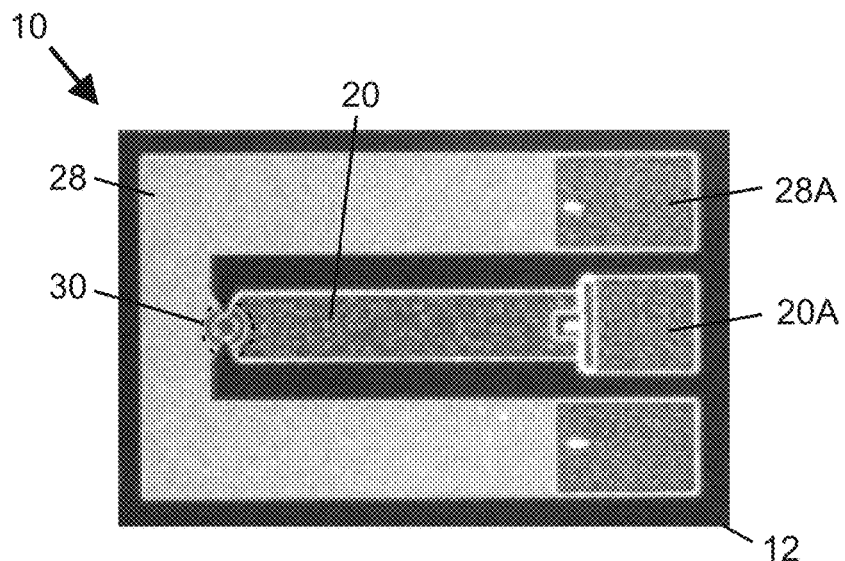
FIG. 12 is a top plan view photograph of a bulk acoustic wave MEMS resonator device suitable for receiving a hermeticity layer, an interface layer, a self-assembled monolayer, and functionalization (e.g. specific binding) material as disclosed herein.

FIG. 12 is a top plan view photograph of a bulk acoustic wave MEMS resonator device 10 (consistent with the portion of the resonator device 10 illustrated in FIG. 1) suitable for receiving a hermeticity layer, an interface layer, a self-assembled monolayer, and/or functionalization (e.g., specific binding) material as disclosed herein, with a top side electrode that may embody or be overlaid with a patterned enhanced surface area element. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is arranged between overlapping portions of the top side electrode 28 and the bottom side electrode 20. Externally accessible contacts 20A, 28A are in electrical communication with the bottom side electrode 20 and the top side electrode 28, respectively. After portions of the resonator device 10 are overlaid with an interface layer, a self-assembled monolayer, and functionalization (e.g., specific binding) material as disclosed herein, the resonator device 10 may be used as a sensor and/or incorporated into a microfluidic device. If desired, multiple resonator devices 10 may be provided in an array on a single substrate 12.

Figure 13:
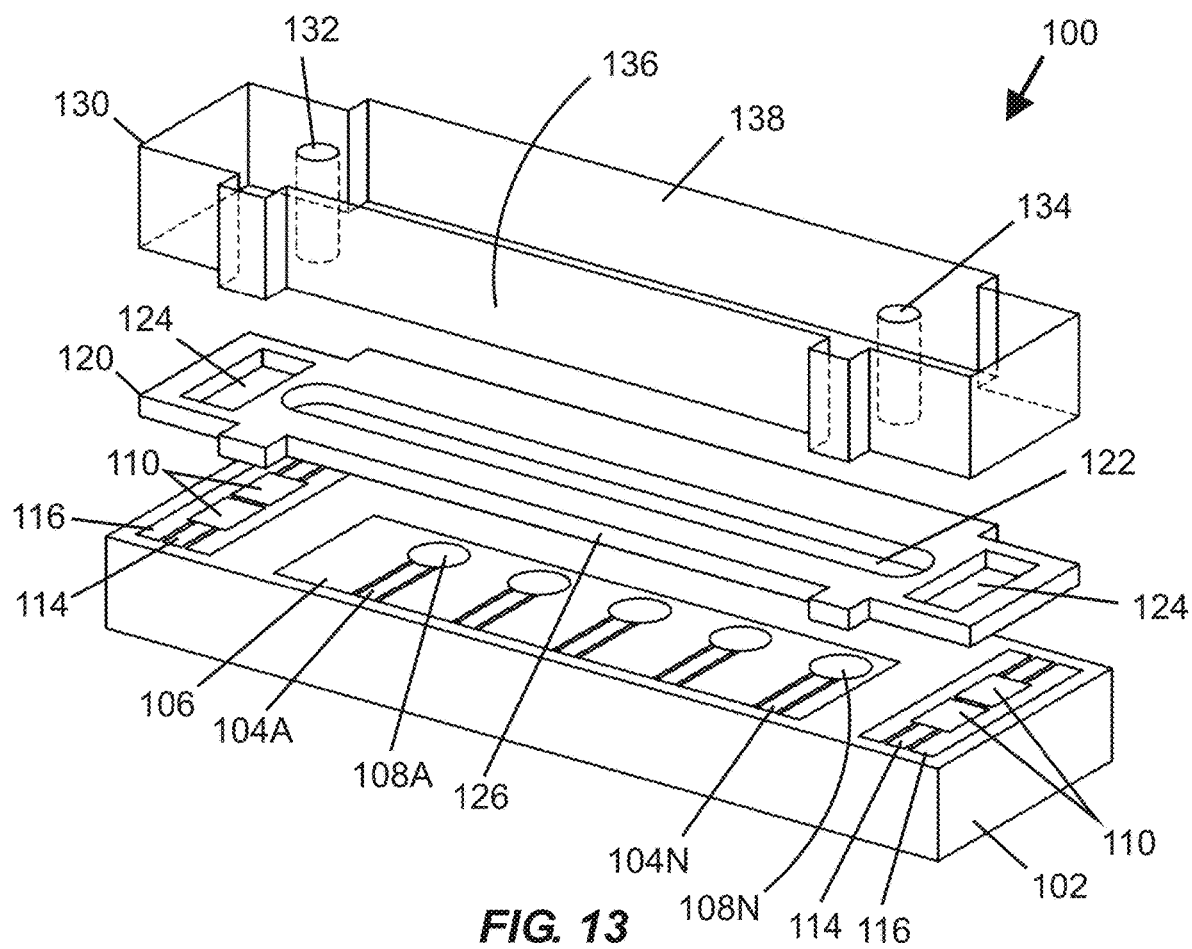
FIG. 13 is a perspective assembly view of a microfluidic device incorporating a substrate with multiple bulk acoustic wave MEMS resonator devices as disclosed herein, an intermediate layer defining a channel containing active regions of the MEMS resonator devices, and a cover or cap layer.

FIG. 13 is a perspective assembly view of a microfluidic device 100 incorporating a substrate 102 with multiple bulk acoustic wave MEMS resonator devices, an intermediate layer 120 defining a central microfluidic channel 122 registered with active regions 108A-108N of the MEMS resonator devices, and a cover or cap layer 130 arranged to cover the intermediate layer 120. Top central portions of the substrate 102, which includes an acoustic reflector (not shown) and a piezoelectric material (not shown), include a top side electrode 106 and bottom side electrodes 104A-104N. Regions in which the foregoing electrodes overlap one another and sandwich the piezoelectric material embody active regions 108A-108N. Preferably, each active region 108A-108N includes at least one patterned enhanced surface area element as disclosed herein. Any suitable number of active regions 108A-108N may be provided and fluidically arranged in series or parallel, although five active regions are illustrated in FIG. 13. Top peripheral (or top end) portions of the substrate 102 further include reference top side electrodes 116 and reference bottom side electrodes 114 in communication with reference overlap regions 110. Such reference overlap regions 110 are not exposed to fluid, and are present to provide a basis for comparing signals obtained from the active regions 108A-108N exposed to fluid within the central microfluidic channel 122. The substrate 102 is overlaid with the intermediate (e.g., wall-defining) layer 120, wherein the central microfluidic channel 122 is intended to receive fluid, and defines peripheral chambers 124 arranged to overlie the reference overlap regions 110 in a sealed fashion. The intermediate layer 120 may be formed of any suitable material such as SU-8 negative epoxy resist, other photoimageable material, or laser-cut "stencil" layers of thin polymeric materials optionally including one or more self-adhesive surfaces (e.g., adhesive tape), etc. The intermediate layer 120 further includes a lateral inset region 126 that enables lateral portions of the top side electrode 106 and bottom side electrodes 104A-104N to be accessed upon assembly of the microfluidic device 100. The cover or cap layer 130 includes a lateral inset region 136 registered with the lateral inset region 126 of the intermediate layer 120, and includes microfluidic ports 132, 134 accessible along a top surface 138 of the cover or cap layer 130 and registered with end portions of the central microfluidic channel 122 defined in the intermediate layer 120 to permit fluid (e.g., liquid) to be supplied to the central microfluidic channel 122 over the active regions 108A-108N. Preferably, at least the electrodes 104A-104N, 106 are overlaid with a hermeticity layer, an interface layer, a self-assembled monolayer, and functionalization (e.g., specific binding) material as disclosed herein. Microfluidic devices according to other configurations may be provided, as will be recognized by those skilled in the art upon review of the present disclosure.

Technical benefits obtainable with various embodiments of the present disclosure may include one or more of the following: enhanced rate of analyte binding to functionalization material overlying an active region of a bulk acoustic wave resonator structure, thereby reducing the time required to complete measurement of a particular sample, and/or enhanced mixing of analyte-containing fluids in fluidic devices incorporating bulk acoustic wave resonator structures, including devices suitable for biosensing or biochemical sensing applications.

Those skilled in the art will recognize improvements and modifications to the preferred embodiments of the present disclosure. All such improvements and modifications are considered within the scope of the concepts disclosed herein and the claims that follow.

What is claimed is:

1. A micro-electrical-mechanical system (MEMS) resonator device comprising:
   a substrate;
   a bulk acoustic wave resonator structure arranged over at least a portion of the substrate, the bulk acoustic wave resonator structure including a piezoelectric material, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region;

at least one functionalization material arranged over at least a portion of the active region; and at least one patterned enhanced surface area element defined within at least a portion of the thickness of the top side electrode and arranged between a lower surface of the top side electrode and the at least one functionalization material, wherein the at least one patterned enhanced surface area element is configured to increase non-planarity of the at least one functionalization material.

2. The MEMS resonator device of claim 1, wherein the at least one patterned enhanced surface area element comprises at least one of (i) a plurality of upwardly protruding portions of the top side electrode or (ii) a plurality of recesses defined in the top side electrode.

3. The MEMS resonator device of claim 1, wherein the top side electrode comprises a non-noble metal, and the MEMS resonator device further comprises a hermeticity layer arranged between the top side electrode and the at least one functionalization material.

4. The MEMS resonator device of claim 1, further comprising an interface layer arranged between the top side electrode and the at least one functionalization material.

5. The MEMS resonator device of claim 1, wherein the at least one patterned enhanced surface area element comprises an electrically conductive material.

6. The MEMS resonator device of claim 1, further comprising a self-assembled monolayer arranged between the top side electrode and the at least one functionalization material.

7. The MEMS resonator device of claim 1, wherein the piezoelectric material comprises a hexagonal crystal structure piezoelectric material comprising a c-axis having an orientation distribution that is predominantly non-parallel to normal of a face of the substrate.

8. The MEMS resonator device of claim 1, wherein:
a peripheral boundary of the active region defines a two-dimensional area; and
the at least one functionalization material is arranged over the at least one patterned enhanced surface area element over a surface area that is at least 10% greater than the two-dimensional area.

9. A fluidic device comprising the MEMS resonator device of claim 1, and a fluidic passage extending over the active region and arranged to conduct a flow of liquid to contact the at least one functionalization material.

10. A method of biological or chemical sensing, the method comprising:
supplying a fluid containing an analyte into a fluidic passage of a fluidic device, the fluidic device comprising:
a MEMS resonator device comprising:
a substrate;
a bulk acoustic wave resonator structure arranged over at least a portion of the substrate, the bulk acoustic wave resonator structure including a piezoelectric material, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region; and at least one functionalization material arranged over at least a portion of the active region; and at least one patterned enhanced surface area element defined within at least a portion of the thickness of the top side electrode and arranged between a lower surface of the top side electrode and the at least one functionalization material, the at least one patterned enhanced surface area configured to increase non-planarity of the at least one functionalization material; and a fluidic passage extending over the active region and arranged to conduct a flow of liquid to contact the at least one functionalization material along the at least one patterned enhanced surface area element, wherein said supplying the fluid includes supplying the fluid into the fluidic passage to cause at least some of the analyte to bind to the at least one functionalization material;

inducing a bulk acoustic wave in the active region; and sensing a change in at least one of a frequency property, a phase property, or an amplitude magnitude property of the bulk acoustic wave resonator structure to indicate at least one of presence or quantity of analyte bound to the at least one functionalization material.

11. A method for fabricating a micro-electrical-mechanical system (MEMS) resonator device comprising an active region and at least one functionalization material arranged over at least a portion of the active region, the method comprising:
forming a top side electrode over a portion of a piezoelectric material arranged over a substrate, with a bottom side electrode being arranged between the piezoelectric material and the substrate, wherein a portion of the piezoelectric material is arranged between the top side electrode and the bottom side electrode to form the active region;

defining at least one patterned enhanced surface area element defined within at least a portion of the thickness of the top side electrode and arranged between a lower surface of the top side electrode and the at least one functionalization material, wherein at least a portion of the at least one patterned enhanced surface area element is registered with the active region; and depositing the at least one functionalization material over the at least one patterned enhanced surface area element, wherein at least a portion of the at least one functionalization material is registered with the active region, and wherein the at least one patterned enhanced surface area element is configured to increase non-planarity of the at least one functionalization material.

12. The method of claim 11, wherein the defining of at least one patterned enhanced surface area element comprises removing material over or from the top side electrode via a subtractive material removal process.

13. The method of claim 12, wherein the subtractive material removal process comprises etching.

14. The method of claim 11, wherein the defining of at least one patterned enhanced surface area element comprises addition of material over or to the top side electrode via an additive manufacturing process.

15. The method of claim 11, wherein:
a peripheral boundary of the active region defines a two-dimensional area; and the at least one functionalization material is arranged over the at least one patterned enhanced surface area element over a surface area that is at least 10% greater than the two-dimensional area.

16. The method of claim 11, further comprising forming at least one wall over a portion of the MEMS resonator device and defining a fluidic passage containing the active region.

* * * * *